(12) United States Patent
Barnett et al.

(10) Patent No.: US 9,950,992 B2
(45) Date of Patent: Apr. 24, 2018

(54) WATER SOLUBLE HALOANILIDE CALCIUM-RELEASE CALCIUM CHANNEL INHIBITORY COMPOUNDS AND METHODS TO CONTROL BONE EROSION AND INFLAMMATION ASSOCIATED WITH ARTHRITIDES

(71) Applicant: West Virginia University, Morgantown, WV (US)

(72) Inventors: John B. Barnett, Morgantown, WV (US); Bjorn C. Soderberg, Masontown, WV (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 15/457,231

(22) Filed: Mar. 13, 2017

(65) Prior Publication Data
US 2017/0260128 A1    Sep. 14, 2017

Related U.S. Application Data

(60) Provisional application No. 62/307,728, filed on Mar. 14, 2016.

(51) Int. Cl.
*C07C 233/15*    (2006.01)
*C07C 211/52*    (2006.01)

(52) U.S. Cl.
CPC .......... *C07C 233/15* (2013.01); *C07C 211/52* (2013.01)

(58) Field of Classification Search
CPC ............................. C07C 233/15; C07C 211/52
See application file for complete search history.

(56) References Cited

U.S. PATENT DOCUMENTS

| 2002/0127605 A1* | 9/2002 | Hamilton .............. C07C 233/65 435/7.1 |
| 2008/0255250 A1 | 10/2008 | Gomez-Orellana et al. |
| 2013/0303621 A1 | 11/2013 | Barnett |

FOREIGN PATENT DOCUMENTS

WO    8705898    10/1987

OTHER PUBLICATIONS 3,4-Dichloro-N-Methylaniline, SID 165232870, U.S. National Library of Medicine, National Center for Biotechnology Information, PubChem, pp. 1-5, Nov. 20, 2013.
Jefjrekvjyacnk-Uhfffaoysa-N, SID 223776872, U.S. National Library of Medicine, National Center for Biotechnology Information, PubChem, pp. 1-7. Feb. 2, 2015.
458C68E3910EA61E401D81C8433954CB, SID 129518465,U.S. National Library of Medicine, National Center for Biotechnology Information, PubChem, pp. 1-7, Dec. 14, 2011.
Till, S.H. et al., Assessment, Investigation, and Management of Acute Monoarthritis, J. Accid Emerg. Med., 1999, vol. 16, 355-61.
Gaffo, A., et al., Treatment of Rheumatoid Arthritis, Am. J. Health Syst. Pharm., 2006, vol. 63, 2451-2465.
Yaroslavskiy, B.B. et al., Functional Osteoclast Attachment Requires Inositol-1,4,5-trisphosphate Receptor-associated cGMP-dependent Kinase Substrate, Lab Invest., 2010, vol. 90, 1533-1542.
Niegishi-Koga, T. et al., CA2+-NFATcl Signaling is an Essential Axis of Osteoclast Differentiation, Immunol. Rev., 2009, vol. 231, 241-256.
Zhou, Y. et al The Role of Calcium Release Activated Calcium Channels in Osteoclast Differentiation, J. Cell. Physiol, 2011, vol. 226, 1082-1089.
Yue, C. et al., Control of Type 1 Interferon-induced Cell Death by Orail-Mediated Calcium Entry in T Cells, J. Biol. Chem., 2012, vol. 287, 3207-3216.
Robinson, L. J. et al., Gene Disruption of the Calcium Channel Orail Results in Inhibition of Osteoclast and Osteoblast Differentiation and Impairs Skeletal Development, Lab. Invest., 2012, vol. 92, 1071-1083.
Soboloff, J. et al., STIM Proteins: Dynamic Calcium Signal Transducers, Nat. Rev. Mol. Cell. Biol., 2012, vol. 13, 549-565.
Qu, B. et al., ORAI-Mediated Calcium Influx in T Cell Proliferation, Apoptosis and Tolerance, Cell Calcium, 2011, vol. 50, 261-269.
Corsini, E. et al., Immunomodulatory Effects of the Herbicide Propanil on Cytokine Production in Humans; In Vivo and In Vitro Exposure, Toxicol. Appl. Pharmacol., 2007, vol. 222, 202-210.
Ranasinghe, P. et al., Exchange Transfusion Can be Life-Saving in Severe Propanil Poisoning: A Case Report, BMC Res. Notes, 2014, vol. 7, 700.
Clutter, S.D. et al., Follistatin-Like Protein 1 Promotes Arthritis by Up-Regulating IFN-Gamma, J. Immunol., 2009, vol. 182, 234-239.
Cackowski, F.C. et al., Osteoclasts are Important for Bone Angiogenesis, Blood, 2010, vol. 115, 140-149.
Tondelli, B. et al., Fetal Liver Cells Transplanted in Utero Rescue the Osteopetrotic Phenotype in the oc/oc Mouse, Am. J. Pathol., 2009, vol. 174, 727-735.

(Continued)

*Primary Examiner* — Pancham Bakshi
(74) *Attorney, Agent, or Firm* — Buchanan Ingersoll & Rooney PC; Craig G. Cochenour

(57) ABSTRACT

A compound that is selected from the group consisting of 3-(3,4-dichloroanilino)-3-oxopropanoic acid (hereinafter "DCOPA"); N-methyl-DCOPA; N,2-dimethyl-DCOPA; 2-methyl-DCOPA; isobutyl-DCOPA; N-methyl-isobutyl DCOPA; 3-(3,4-bibromoanilino)-3-oxopropanoic acid; and analogs of DCOPA; and analogs of 3-(3,4-bibromoanilino)-3-oxopropanoic acid; and pharmaceutically acceptable salts of these compounds, are disclosed. A method of controlling bone erosion in a patient comprising administering to the patient a therapeutically effective amount of at least one of these compounds, or a pharmaceutically acceptable salt of at least one of these compounds, is provided. A method of reducing inflammation in a patient having an inflammatory condition comprising administering to the patient a therapeutically effective amount of at least one of these compounds, or a pharmaceutically acceptable salt of at least one of these compounds is provided.

1 Claim, 15 Drawing Sheets

(56) References Cited

OTHER PUBLICATIONS

Prakriya, M. et al., Orail is an Essential Pore Subunit of the CRAC Channel, Nature, 2006, vol. 443, 230-233.
Roberts-Thomson, S.J. et al., ORAI-mediated Calcium Entry: Mechanism and Roles, Diseases and Pharmacology, Pharmacol. Ther., 2010, vol. 127, 121-130.
Endo, Y. et al., Dominant Mutations in ORAI1 Cause Tubular Aggrtegate Myophathy with Hypocalcemia Via Constitutive Activation of Store-Operated Ca2+ Channels, Hum. Mol. Genet., Sep. 16, 2014, Epub ahead of print.
Hwang, D.Y. et al., Genetic Polymorphisms of ORAI1 and Chronic Kidney Disease in Taiwanese Population, Biomed. Res. Int., 2014, 290863.
Misceo, D. et al., A Dominant STIM1 Mutation Causes Stormorken Syndrome, Hum. Mutat., 2014, vol. 35, 556-564.
Samanta, K. et al., Key Role for Store-Operated Ca2+ Channels in Activating Gene Expression in Human Airway Bronchial Epithelial Cells, PLoS One, 2014, vol. 9 : el 05586.
Somasundaram, A. et al., Store-Operated CRAC Channels Regulate Gene Expression and Proliferation in Neural Progenitor Cells, J. Neurosci., 2014, vol. 34, 9107-9123.
Song, S.S. et al., BF02, a Recombinant TNFR2 Fusion Protein, Alleviates Adjuvant Arthritis by Regulating T Lymphocytes in Rats, Acta. Pharmacol. Sin., 2013, vol. 34, 414-423.
Criado, G. et al., Alternative p38 MAPKs are Essential for Collagen-Induced Arthritis, Arthritis Rheumatol., 2014, vol. 66, 1208-1217.
Marijnissen, R.J. et al., Interleukin-21 Receptor Deficiency Increases the Initial Toll-Like Receptor 2 Response but Protects Against Joint Pathology by Reducing Th1 and Th17 Cells During Streptococcal Cell Wall Arthritis, Arthritis Rheumatol., 2014, vol. 66, 886-895.
Raychaudhuri, S.P., Role of IL-17 in Psoriasis and Psoriatic Arthritis, Clin. Rev. Allergy Immunol., 2013, vol. 44, 183-193.
Li, J. et al., The Dynamic Duo-Inflammatory M1 Macrophages and Th17 Cells in Rheumatic Diseases, J. Orthop. Rheumatol., 2013, vol. 1, 4.
Kim, K.D. et al., Calcium Signaling Via Orail is Essential for Induction of the Nuclear Oiphan Receptor Pathway to Drive Th17 Differentiation, J. Immunol., 2014, vol. 192, 110-122.
Muller, S. et al., The Endolysosomal Cysteine Cathepsins L and K are Involved in Macrophage-Mediated Clearance of *Staphylococcus aureus* and the Concomitant Cytokine Induction, FASEB J., 2014, vol. 281, 162-175.
Kehely, A. et al., Circulating Levels of Tartrate-Resistant Acid Phosphatase in Macrophage-Activated Lung Disease, Ann. Clin. Biochem., 1992, vol. 29, 172-175.
Gao, X. et al., A Store-Operated Calcium Channel Inhibitor Attenuates Collagen-Induced Arthritis, Br. J. Pharmacol., Feb. 5, 2015, doi: 10.1111/bph.13104, (Epub ahead of print).
Takezawa, R. et al., A Pyrazole Derivative Potently Inhibits Lymphocyte Ca2+ Influx and Cytokine Production by Facilitating Transient Receptor Potential Melastatin 4 Channel Activity, Mol. Pharmacol., vol. 69, 1413-1420.
The International Search Report and the Written Opinion of the International Searching Authority dated May 25, 2017 for PCT/US2017/022083 filed Mar. 13, 2017.

* cited by examiner

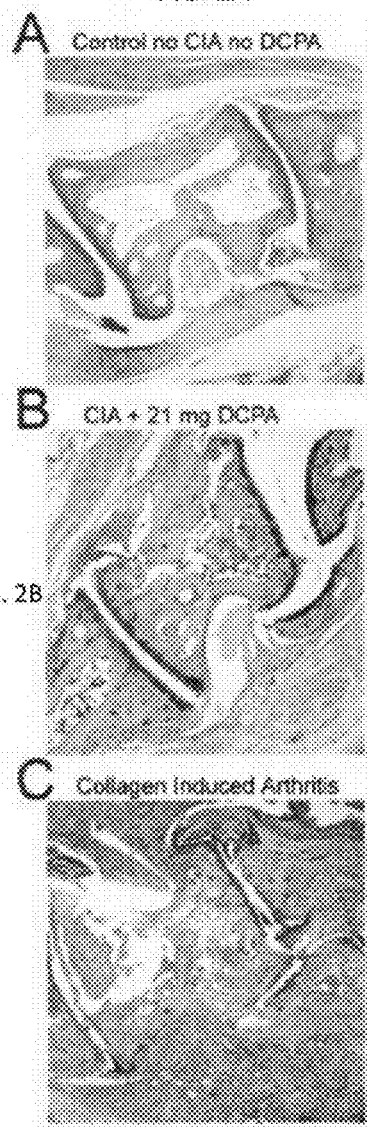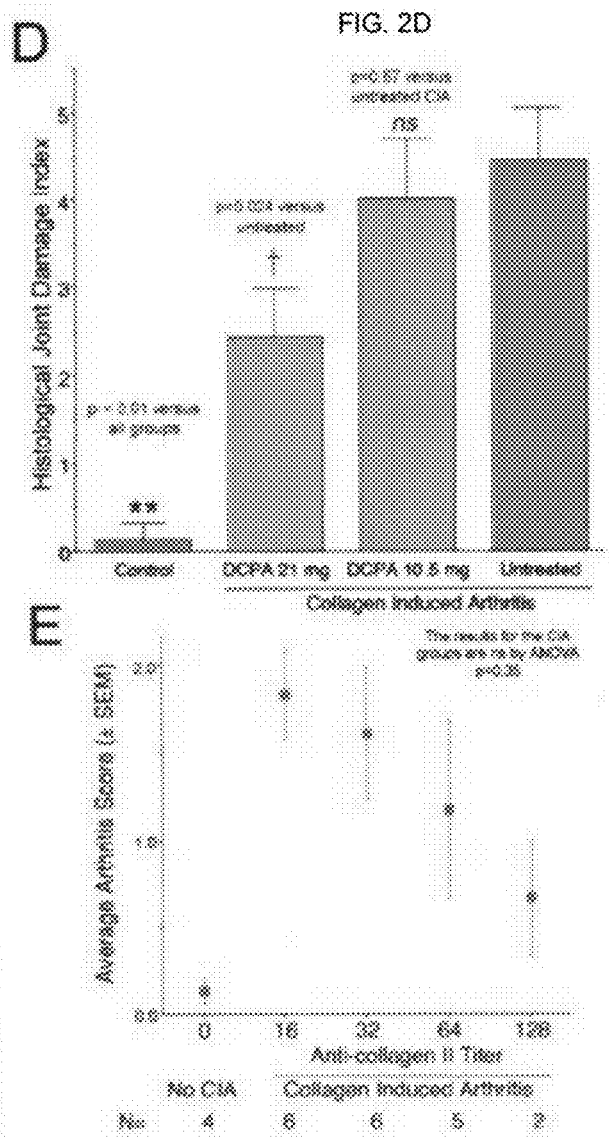

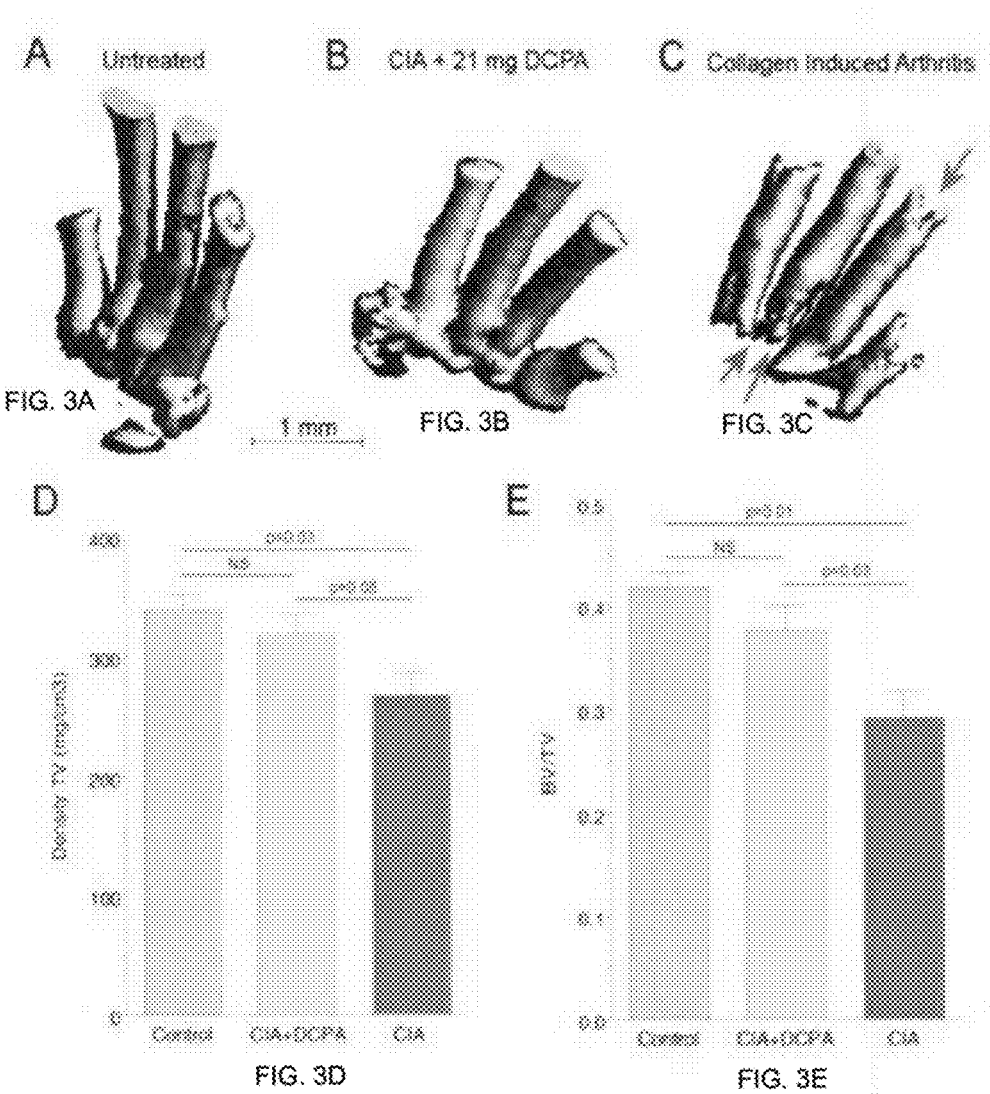

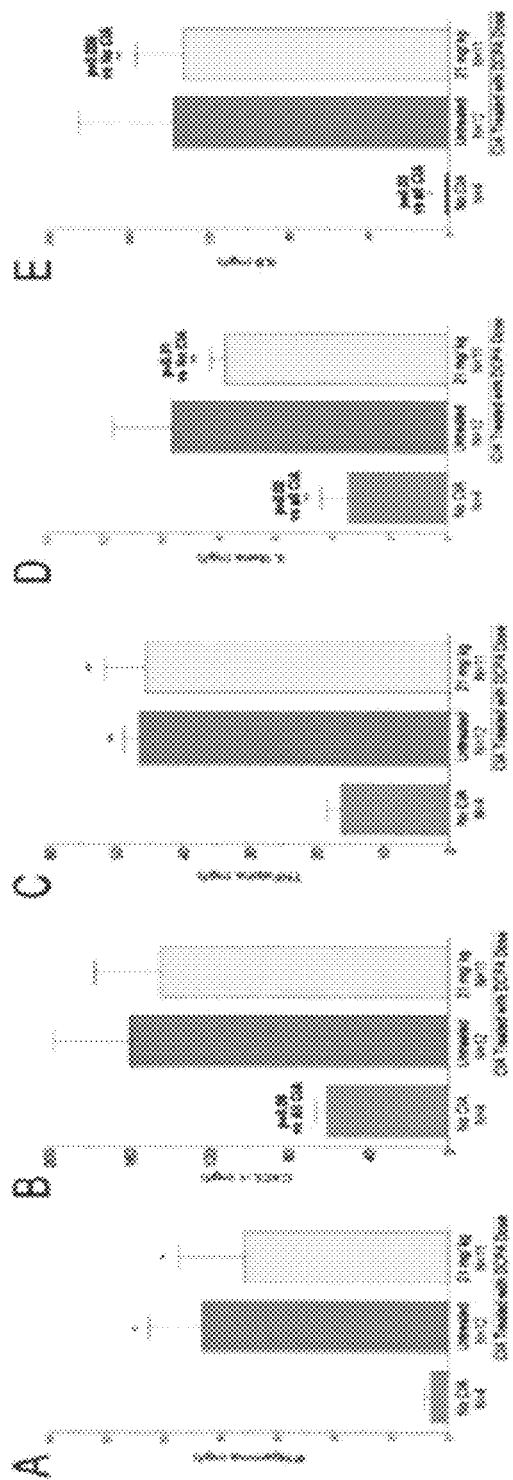

FIG. 5A
TCIRG/ATPa3
A Control no CIA
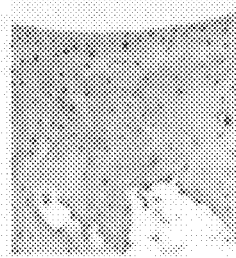
B CIA + 21 mg DCPA
FIG. 5B
C CIA Untreated
FIG. 5C
FIG. 5D
TCIRG/ATPa3
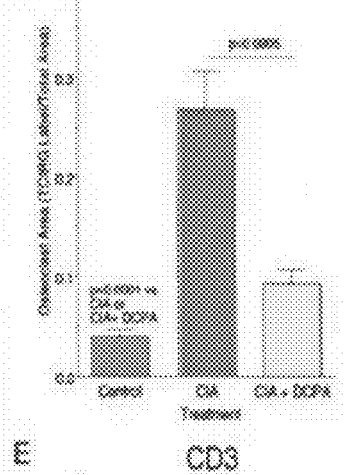
D
E CD3
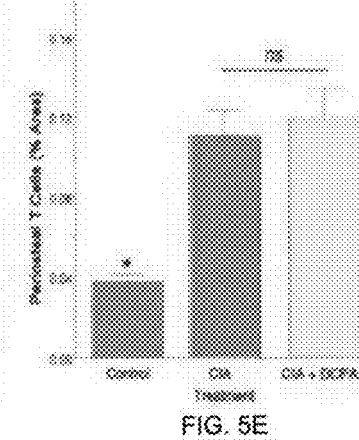
FIG. 5E
FIG. 5F
CD3
F Control no CIA
G CIA + 21 mg DCPA
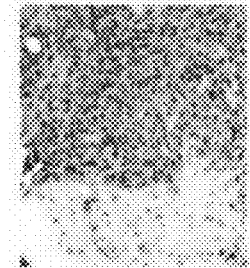
FIG. 5G
H CIA Untreated
FIG. 5H

| AVERAGES | PI Only | PI and Annexin V | Negative | Annexin V Only |
|---|---|---|---|---|
| Unstained | 0.0 | 0.0 | 100.0 | 0.0 |
| Annexin V Control | 0.0 | 0.0 | 98.5 | 1.5 |
| PI Control | 54.4 | 0.0 | 45.6 | 0.0 |
| None | 1.6 | 3.2 | 91.9 | 3.3 |
| EtOH | 2.2 | 1.7 | 93.9 | 2.1 |
| DCPA 800 | 6.4 | 92.4 | 0.8 | 0.4 |
| NMDCOPA 800 | 1.9 | 2.2 | 93.9 | 1.9 |
| DCPA 400 | 6.8 | 27.6 | 64.2 | 1.5 |
| NMDCOPA 400 | 1.6 | 2.1 | 93.9 | 2.4 |
| DCPA 200 | 4.0 | 11.2 | 82.5 | 2.3 |
| NMDCOPA 200 | 1.9 | 2.1 | 93.1 | 2.9 |
| DCPA 100 | 2.7 | 3.1 | 92.4 | 1.8 |
| NMDCOPA 100 | 1.8 | 2.1 | 93.9 | 2.1 |
| DCPA 50 | 2.5 | 1.9 | 94.4 | 1.3 |
| NMDCOPA 50 | 2.3 | 2.1 | 94.2 | 1.4 |
| DCPA 25 | 3.6 | 2.4 | 92.7 | 1.3 |
| NMDCOPA 25 | 1.9 | 2.2 | 94.8 | 1.2 |
| DCPA 12.5 | 1.9 | 2.0 | 94.7 | 1.3 |
| NMDCOPA 12.5 | 2.0 | 2.2 | 94.6 | 1.2 |

WATER SOLUBLE HALOANILIDE CALCIUM-RELEASE CALCIUM CHANNEL INHIBITORY COMPOUNDS AND METHODS TO CONTROL BONE EROSION AND INFLAMMATION ASSOCIATED WITH ARTHRITIDES

CROSS-REFERENCE TO RELATED APPLICATIONS

This utility patent application claims the benefit of U.S. Provisional Patent Application Ser. No. 62/307,728, filed on Mar. 14, 2016. The entire contents of U.S. Provisional Patent Application Ser. No. 62/307,728 is incorporated by reference into this utility patent application as if fully written herein.

BACKGROUND OF THE INVENTION

Field of the Invention

We have shown previously that analogs of DCPA retain the ability to block calcium-release activate calcium (CRAC) channels as the parent compound DCPA (N-(3,4-dichlorophenyl)propanamide) but by design, are not metabolized to more toxic N—OH or 6-OH metabolites of the parent compound. The difficulty with these compounds is that they are not water soluble and this makes development of a drug delivery modality more challenging. The compounds of this patent application have been modified at the amide chain with a hydrogen bond acceptor or ionizable functional group like an acid. A compound of this Application is at least one compound selected from the group consisting of 3-(3,4-dichloroanilino)-3-oxopropanoic acid (hereinafter "DCOPA"); N-methyl-DCOPA; N,2-dimethyl-DCOPA; 2-methyl-DCOPA; isobutyl-DCOPA; N-methyl-isobutyl DCOPA; 3-(3,4-bibromoanilino)-3-oxopropanoic acid; and analogs of DCOPA; and analogs of 3-(3,4-dibromoanilino)-3-oxopropanoic acid; and pharmaceutically acceptable salts of these compounds. DCOPA is a more water soluble compound than DCPA. These new compounds of this application inhibit CRAC channels and thus, inhibit osteoclast development and subsequent bone erosion associated with arthritides. Because these new compounds of this application have enhanced solubility, drug delivery will be simplified without sacrificing efficacy. There is currently no drug available to inhibit bone erosion by down-regulating osteoclast development. Bone erosion is the cause of major debilitating effects of arthritides. The compounds of this Application meet this unmet need.

Description of the Background Art

The role of calcium release activated calcium (CRAC) channels is discussed in Zhou et al., "The role of calcium release activated calcium channels in osteoclast differentiation", J. Cell Physiol 226:1082 (2011).

Analogs of DCPA that inhibit CRAC channels is the subject of a previously filed patent application by WVU, namely, U.S. patent application Ser. No. 13/864,438, filed on Apr. 17, 2013, US Patent Application Publication No. 2013/0303621 A1, having a publication date of Nov. 14, 2013. We have shown that the parent compound, DCPA. inhibits CRAC channels and inhibits development of osteoclasts, significantly reduces the severity of collagen-induced arthritis (CIA) in mice, and inhibits the blood destruction associated with CIA. DCPA and its analogs, e.g., N-methyl-DCPA, are very hydrophobic which presents challenges to developing a drug using these compounds. In comparison to known compounds, the compounds of this patent application are designed having greater solubility while retaining biological activity.

Many thousands of people suffer from various forms of arthritis secondary to inflammatory processes that destroy bone and joints, including rheumatoid arthritis (RA), juvenile RA, arthritis secondary to infections, and idiopathic arthritis. Treatments available for these conditions include anti-inflammatory drugs, e.g., etanercept, antimetabolites, e.g., methotrexate and nonsteroidal anti-inflammatory drugs (NSAIDs, for example ibuprofen) which have significant side effects. However, none of these drugs are effective at preventing bone erosion that occurs in a significant percentage of arthritis patients

SUMMARY OF THE INVENTION

The present invention provides a compound that is 3,4-Dichloro-N-methylaniline.

In another embodiment of this invention, a compound is provided that is 3-[3,4-dichlorophenyl)methylamino]-3-oxopropanoic acid.

In another embodiment of this invention, a compound is provided that is 3-(3,4-dichloroanilino)-3-oxopropanoic acid.

In another embodiment of this invention, a compound is provided that is 3,4-dibromo-N-methylaniline.

In another embodiment of this invention, a compound is provided that is 3-[3,4-dibromophenyl)methylamino]-3-oxopropanoic acid.

In another embodiment of this invention, a compound is provided that is 3-(3,4-dibromoanilino)-3-oxopropanoic acid.

In another embodiment of this invention, a compound is provided that is selected from the group consisting of 3-(3,4-dichloroanilino)-3-oxopropanoic acid (hereinafter "DCOPA"); N-methyl-DCOPA; N,2-dimethyl-DCOPA; 2-methyl-DCOPA; isobutyl-DCOPA; N-methyl-isobutyl DCOPA; and 3-(3,4-bibromoanilino)-3-oxopropanoic acid.

Another embodiment of this invention provides a compound that is an analog of DCOPA.

Another embodiment of this invention provides a compound that is an analog of 3-(3,4-dibromoanilino)-3-oxopropanoic acid.

Another embodiment of this invention provides a method of controlling bone erosion in a patient comprising administering to a patient a therapeutically effective amount of at least one compound selected from the group consisting of 3-(3,4-dichloroanilino)-3-oxopropanoic acid (hereinafter "DCOPA"); N-methyl-DCOPA; N,2-dimethyl-DCOPA; 2-methyl-DCOPA; isobutyl-DCOPA; N-methyl-isobutyl DCOPA; and 3-(3,4-dibromoanilino)-3-oxopropanoic acid.

Another embodiment of this invention provides a method of controlling bone erosion in a patient comprising administering to a patient a therapeutically effective amount of at least one compound that is an analogs of DCOPA or an analog of 3-(3,4-dibromoanilino)-3-oxopropanoic acid.

Another embodiment of this invention provides a method of controlling bone erosion in a patient comprising including administering to said patient a therapeutically effective amount of a pharmaceutically acceptable salt of at least one compound selected from the group consisting of 3-(3,4-dichloroanilino)-3-oxopropanoic acid (hereinafter "DCOPA"); N-methyl-DCOPA; N,2-dimethyl-DCOPA; 2-methyl-DCOPA; isobutyl-DCOPA; N-methyl-isobutyl DCOPA; and 3-(3,4-dibromoanilino)-3-oxopropanoic acid.

In a preferred embodiment of this invention, a method of controlling bone erosion in a patient is provided comprising administering to the patient a therapeutically effective amount of a compound that is a 3-[3,4-dichlorophenyl) methylamino]-3-oxopropanoic acid, 3-(3,4-dichloroanilino)-3-oxopropanoic acid, 3-(3,4-dibromoanilino)-3-oxopropanoic acid, or 3-[3,4-dibromophenyl)methylamino]-3-oxopropanoic acid.

Another embodiment of this invention provides a method of reducing inflammation in a patient having an inflammatory condition comprising administering to the patient a therapeutically effective amount of a compound selected from the group consisting of 3-(3,4-dichloroanilino)-3-oxopropanoic acid (hereinafter "DCOPA"); N-methyl-DCOPA; N,2-dimethyl-DCOPA; 2-methyl-DCOPA; isobutyl-DCOPA; N-methyl-isobutyl DCOPA; and 3-(3,4-dibromoanilino)-3-oxopropanoic acid.

Another embodiment of this invention provides a method of reducing inflammation in a patient having an inflammatory condition comprising administering to the patient a therapeutically effective amount of an analog of DCOPA or an analog of 3-(3,4-dibromoanilino)-3-oxopropanoic acid.

Another embodiment of this invention provides a method of reducing inflammation in a patient having an inflammatory condition comprising administering to the patient a therapeutically effective amount of a pharmaceutically acceptable salt of a compound selected from the group consisting of 3-(3,4-dichloroanilino)-3-oxopropanoic acid (hereinafter "DCOPA"); N-methyl-DCOPA; N,2-dimethyl-DCOPA; 2-methyl-DCOPA; isobutyl-DCOPA; N-methyl-isobutyl DCOPA; and 3-(3,4-dibromoanilino)-3-oxopropanoic acid.

In preferred embodiment of this invention, a method of reducing inflammation in a patient having an inflammatory condition is provided comprising administering to the patient a therapeutically effective amount of a compound that is 3-[3,4-dichlorophenyl)methylamino]-3-oxopropanoic acid, 3-(3,4-dichloroanilino)-3-oxopropanoic acid, 3-(3,4-dibromoanilino)-3-oxopropanoic acid, or 3-[3,4-dibromophenyl)methylamino]-3-oxopropanoic acid.

In preferred embodiment of this invention, a method of reducing inflammation in a patient having an inflammatory condition is provided comprising administering to the patient a therapeutically effective amount of a pharmaceutically acceptable salt of a compound that is 3-[3,4-dichlorophenyl)methylamino]-3-oxopropanoic acid, 3-(3,4-dichloroanilino)-3-oxopropanoic acid, 3-(3,4-dibromoanilino)-3-oxopropanoic acid, or 3-[3,4-dibromophenyl)methylamino]-3-oxopropanoic acid.

BRIEF DESCRIPTION OF THE DRAWINGS

FIG. 1A shows the median effect relative to CIA/placebo (top trace) and untreated controls (lower trace). There is a trend toward efficacy at intermediate times in 10.5 mg/kg/d but only the 21 mg/kg/day dose had a durable effect. The data were gathered by a blinded observer. N=4 for untreated controls; N=11 for CIA/placebo; N=10 for the low dose CIA/DCPA treated group; N=8 for the high doses CIA/DCPA treated group. Error bars are omitted for clarity; CIA/placebo was statistically different from high dose CIA/DCPA by ANOVA ($p<0.01$) and different from the CIA/placebo controls ($p<0.001$).

FIG. 1B is a scatter plot showing the arthritis scores at Day 37. This demonstrates that >50% animals in the placebo and low dose CIA/DCPA group show arthritis scores that exceed the mean and several animals showed the maximum arthritis score, whereas a majority of the animals in the high dose CIA/DCPA group showed no or minimal arthritis scores.

FIG. 2A shows the effect of DCPA treatment on collagen induced arthritis at 40 days of an ankle bone in an untreated animal (without CIA, histological score 0).

FIG. 2B shows the effect of DCPA treatment on collagen induced arthritis at 40 days of an ankle bone of an animal after high dose CIA/DCPA (21 mg DCPA). FIG. 2B shows that there is inflammation, with synovial thickening, but it is not severe (Histological damage score 4).

FIG. 2C shows the effect of DCPA treatment on collagen induced arthritis at 40 days of an ankle bone of an animal with severe arthritis in a CIA/placebo, with severe synovial inflammation, pannus in the joint space, and severe bone degradation (Histological damage score 8). All fields are 1.2 mm across.

FIG. 2D shows a histological joint damage index and the effect of DCPA treatment on collagen induced arthritis at 40 days. FIG. 2D shows the severity of arthritis in each group scored by a blinded observer based on sections as in A-C. In all groups, some animals did not develop arthritis (see supplemental Table SI), reducing mean scores. The high dose CIA/DCPA group is statistically different from the CIA/placebo group, $p=0.024$. The untreated group was different from all other groups, $p<0.01$. The low dose group was poorly separated on day 40 histology, and not studied further. Both hind feet of each animal were individually processed and blindly scored, so the number of measurements is twice the number of animals. Mean±SEM, n=8 (untreated, 4 animals), 24 (CIA/placebo 12 animals), or 22 (for either dose of CIA/DCPA 11 animals, one lost during treatment).

FIG. 2E shows the average arthritis score for various anti-type II collagen titers FIG. 2E shows that the anti-type II collagen titer in CIA mice had a median value of 32, and titer was unrelated to severity of arthritis by ANOVA ($p=0.35$). Mean±SEM.

FIG. 3A shows a micro CT showing loss of bone in untreated forelimb metacarpals in untreated mice.

FIG. 3B shows a micro CT of a forelimb metacarpals of mice treated with a high-dose CIA/DCPA (21 mg DCPA).

FIG. 3C shows a micro CT of a forelimb metacarpals of mice in collagen induced arthritis CIA/placebo after sacrifice at day 40. Arrows in FIG. 3C show cortical bone defects.

FIG. 3D shows bone density in total volume of bone for control, CIA+DCPA, and CIA.

FIG. 3E shows bone volume (BV) per total volume (TV) in four controls and nine DCPA treated or untreated animals each. In both cases the CIA has significantly reduced bone; the DCPA treated bone is not different from the untreated control and is statistically greater than CIA in BV/TV.

FIG. 4A shows the effect of CIA and treatment with DCPA on production of key serum inflammatory factor IFN-γ.

FIG. 4B shows the effect of CIA and treatment with DCPA on production of key serum inflammatory factor CXCL1.

FIG. 4C shows the effect of CIA and treatment with DCPA on production of key serum inflammatory factor TNF-α.

FIG. 4D shows the effect of CIA and treatment with DCPA on production of key serum inflammatory factor IL-1β.

FIG. 4E shows the effect of CIA and treatment with DCPA on production of key serum inflammatory factor IL-6.

FIG. 5A shows a section of specimen based on the control on osteoclast bone interface density determined by ATPa3 (TCIRG) antibody labeling, and effect on CD3 T cells.

FIG. 5B shows a section of specimen based on CIA and DCPA (21 mg) on osteoclast bone interface density determined by ATPa3 (TCIRG) antibody labeling, and effect on CD3 T cells.

FIG. 5C shows a section of specimen based on CIA untreated on osteoclast bone interface density determined by ATPa3 (TCIRG) antibody labeling, and effect on CD3 T cells.

FIG. 5D shows a osteoclast area (TCIRG antibody labeling/total area) on blindly scored area of ATPa3 labeling on bone. Mean fraction±SEM; n=5 for untreated and 9 for CIA/placebo or CIA/DCPA treatment (right bar). All groups are statistically different with high confidence.

FIG. 5E shows the effect on CD3 T cells for control, CIA, and CIA and DCPA treated bone. CIA animals have many more T cells per section area, but T cell density in infiltrates is not reduced by DCPA treatment. The DCPA treatment greatly reduces inflammatory volume (FIGS. 1,3) so total T cells will be far fewer.

FIG. 5F shows the effect on CD3 T cells on animal section with CD3 antibody labeling for control no CIA. Note the T cells in the ligaments of a no-CIA animal by the arrow in FIG. 5F.

FIG. 5G shows the effect on CD3 T cells on animal section with CD3 antibody labeling for CIA and 21 mg DCPA treatment.

FIG. 5H shows the effect on CD3 T cells on animal section with CD3 antibody labeling for CIA untreated.

FIG. 10 shows apoptosis data on NMe-DCOPA (i.e. abbreviated NMDCOPA in FIG. 10).

FIG. 11 A shows the fraction of animals with maximal arthritis scores. This demonstrates the efficacy of CIA induction (top trace), and the treatment failure proportion in treated groups.

FIG. 12A shows data of arthritis indices for all animals in one experiment of treatment with placebo (inert composition), 10.5 mg/day DCPA treatment.

FIG. 12B shows data of arthritis indices for all animals in one experiment of treatment with 10.5 mg/day, and 21 mg/day DCPA treatment.

FIG. 13 shows data of histomorphometric indices from micro computed tomography of controls and no CIA, CIA and 21 mg DCPA treatment, and CIA and untreated group of animals.

DESCRIPTION OF THE PREFERRED EMBODIMENTS

Figure 1A:
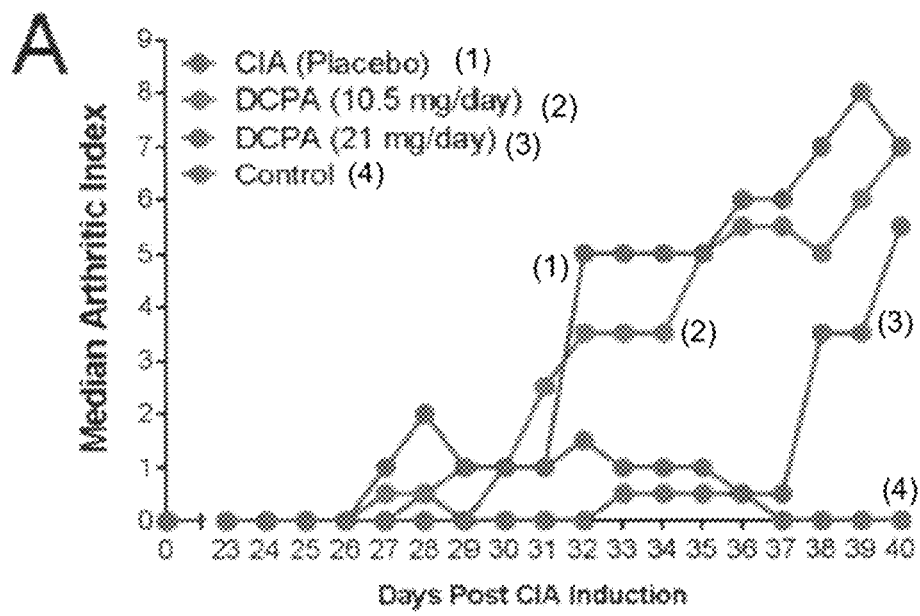
FIG. 1A shows the median effect of DCPA treatment by continuous-release subcutaneous pellets on collagen-induced arthritis as measured by the arthritic index.

The present invention provides a compound that is 3,4-Dichloro-N-methylaniline.

In another embodiment of this invention, a compound is provided that is 3-[3,4-dichlorophenyl)methylamino]-3-oxopropanoic acid.

A preferred embodiment of this invention provides a compound that is 3-(3,4-dichloroanilino)-3-oxopropanoic acid.

In another embodiment of this invention, a compound is provided that is 3,4-dibromo-N-methylaniline.

Another embodiment of this invention provides a compound that is 3-[3,4-dibromophenyl)methyl amino]-3-oxopropanoic acid.

In another preferred embodiment of this invention, a compound is provided that is 3-(3,4-dibromoanilino)-3-oxopropanoic acid.

In another embodiment of this invention, a compound is provided that is selected from the group consisting of 3-(3,4-dichloroanilino)-3-oxopropanoic acid (hereinafter "DCOPA"); N-methyl-DCOPA; N,2-dimethyl-DCOPA; 2-methyl-DCOPA; isobutyl-DCOPA; N-methyl-isobutyl DCOPA; and 3-(3,4-bibromoanilino)-3-oxopropanoic acid.

Another embodiment of this invention provides a compound that is an analog of DCOPA, or an analog of 3-(3,4-dibromoanilino)-3-oxopropanoic acid.

Another embodiment of this invention provides a method of controlling bone erosion in a patient comprising administering to a patient a therapeutically effective amount of at least one compound selected from the group consisting of 3-(3,4-dichloroanilino)-3-oxopropanoic acid (hereinafter "DCOPA"); N-methyl-DCOPA; N,2-dimethyl-DCOPA; 2-methyl-DCOPA; isobutyl-DCOPA; N-methyl-isobutyl DCOPA; and 3-(3,4-dibromoanilino)-3-oxopropanoic acid.

Another embodiment of this invention provides a method of controlling bone erosion in a patient comprising administering to a patient a therapeutically effective amount of at least one compound that is an analog of DCOPA or an analog of 3-(3,4-dibromoanilino)-3-oxopropanoic acid.

Another embodiment of this invention provides a method of controlling bone erosion in a patient comprising including administering to said patient a therapeutically effective amount of a pharmaceutically acceptable salt of at least one compound selected from the group consisting of 3-(3,4-dichloroanilino)-3-oxopropanoic acid (hereinafter "DCOPA"); N-methyl-DCOPA; N,2-dimethyl-DCOPA; 2-methyl-DCOPA; isobutyl-DCOPA; N-methyl-isobutyl DCOPA; and 3-(3,4-dibromoanilino)-3-oxopropanoic acid.

In a preferred embodiment of this invention, a method of controlling bone erosion in a patient is provided comprising administering to the patient a therapeutically effective amount of a compound that is a 3-[3,4-dichlorophenyl) methylamino]-3-oxopropanoic acid, 3-(3,4-dichloroanilino)-3-oxopropanoic acid, 3-(3,4-dibromoanilino)-3-oxopropanoic acid, or 3-[3,4-dibromophenyl)methylamino]-3-oxopropanoic acid, or a pharmaceutically acceptable salt of at least one of said compounds.

Another embodiment of this invention provides a method of reducing inflammation in a patient having an inflammatory condition comprising administering to the patient a therapeutically effective amount of a compound selected from the group consisting of 3-(3,4-dichloroanilino)-3-oxopropanoic acid (hereinafter "DCOPA"); N-methyl-DCOPA; N,2-dimethyl-DCOPA; 2-methyl-DCOPA; isobutyl-DCOPA; N-methyl-isobutyl DCOPA; and 3-(3,4-dibromoanilino)-3-oxopropanoic acid.

Another embodiment of this invention provides a method of reducing inflammation in a patient having an inflammatory condition comprising administering to the patient a therapeutically effective amount of a compound that is an analog of DCOPA, or an analog of 3-(3,4-dibromoanilino)-3-oxopropanoic acid.

Another embodiment of this invention provides a method of reducing inflammation in a patient having an inflammatory condition comprising administering to the patient a therapeutically effective amount of a pharmaceutically acceptable salt of a compound selected from the group consisting of 3-(3,4-dichloroanilino)-3-oxopropanoic acid (hereinafter "DCOPA"); N-methyl-DCOPA; N,2-dimethyl-DCOPA; 2-methyl-DCOPA; isobutyl-DCOPA; N-methyl-isobutyl DCOPA; and 3-(3,4-dibromoanilino)-3-oxopropanoic acid.

In preferred embodiment of this invention, a method of reducing inflammation in a patient having an inflammatory condition is provided comprising administering to the patient a therapeutically effective amount of a compound that is 3-[3,4-dichlorophenyl)methylamino]-3-oxopropanoic acid, 3-(3,4-dichloroanilino)-3-oxopropanoic acid, 3-(3,4-dibromoanilino)-3-oxopropanoic acid, or 3-[3,4-dibromophenyl)methylamino]-3-oxopropanoic acid.

In preferred embodiment of this invention, a method of reducing inflammation in a patient having an inflammatory condition is provided comprising administering to the patient a therapeutically effective amount of a pharmaceutically acceptable salt of a compound that is 3-[3,4-dichlorophenyl)methylamino]-3-oxopropanoic acid, 3-(3,4-dichloroanilino)-3-oxopropanoic acid, 3-(3,4-dibromoanilino)-3-oxopropanoic acid, or 3-[3,4-dibromophenyl)methylamino]-3-oxopropanoic acid.

The present compounds have the following advantages over background art compounds:

enhanced solubility which overcomes the challenges of developing a suitable drug delivery mode;

designed to inhibit CRAC channels and thus, many have utility in other biological processes that utilizes this pathway to activation, e.g., inflammation (cytokine production), T cell activation, cancer cell growth and metastasis, etc.

Synthesis Schemes 1. 3,4-Dichloro-N-methylaniline (2)

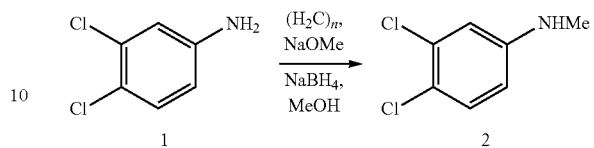

To a solution of 3,4-dichloroaniline (1) (5.00 g, 30.9 mmol) in methanol (100 mL) was added sodium methoxide (12.5 g, 230 mol) and the mixture was poured into a suspension of paraformaldehyde (2.78 g, 92.6 mmol) in methanol (100 mL). The resulting mixture was stirred at ambient temperature under a nitrogen atmosphere until the reaction was complete as monitored by TLC (72 h). Sodium borohydride (2.33 g, 61.7 mmol) was added and the mixture was heated at reflux for 8 h. The reaction was quenched with saturated aqueous ammonium chloride solution (200 mL) and extracted with ethyl acetate (3×200 mL). The combined organic phases were washed with water (200 mL), dried (MgSO$_4$), and filtered. The solvents were removed under reduced pressure at water aspirator pressure and the crude product was purified by flash chromatography on silica gel (ethyl acetate/hexane, 2:98) affording 2 (5.00 g, 28.4 mmol, 92%). $^1$H NMR (400 MHz, CDCl$_3$) □ 7.18 (d, J=8.4 Hz, 1H), 6.65 (d, J=2.8 Hz, 1H), 6.42 (dd, J=8.8 Hz, 2.8 Hz, 1H), 3.78 (brs, 1H), 2.80 (d, J=4.8 Hz, 3H).

2. 3-[3,4-Dichlorophenyl)methylamino]-3-oxopropanoic Acid (5)

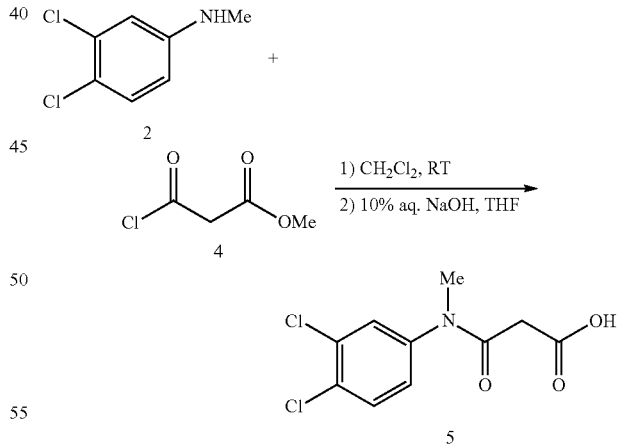

To a solution of 3,4-dichloro-N-methylaniline (2) (2.00 g, 11.4 mmol) in dichloromethane (20 mL) under a nitrogen atmosphere at ambient temperature was added methyl malonyl chloride (1.86 g, 13.6 mmol). The resulting mixture was stirred for 16 h followed by the addition of 2% HCl solution (aq., 20 mL). The mixture was extracted with dichloromethane (3×20 mL), the combined organic phase were dried (Na$_2$SO$_4$), filtered, and the solvent was removed under reduced pressure at water aspirator pressure.

The crude product was dissolved in tetrahydrofuran (40 mL) and treated with 10% aq. NaOH solution (20 mL) and the resulting mixture was stirred at ambient temperature for 6 h. The resulting mixture was washed with ether (3×20 mL) and the aqueous phase was treated with 6N HCl (aq.) until acidic (pH 2, pH paper). The acidic aqueous solution was extracted with ethyl acetate (3×20 mL). The combined organic phases were dried (MgSO$_4$), filtered, and the solvent was removed under reduced pressure at water aspirator pressure to afford pure 3 (2.19 g, 8.36 mmol, 73%).

$^1$H NMR (400 MHz, CDCl$_3$) ☐ 11.58 (brs, 1H), 7.56 (d, J=8.4 Hz, 1H), 7.36 (d, J=2.4 Hz, 1H) 7.10 (dd, J=8.4 Hz, 2.4 Hz, 1H), 3.31 (s, 3H), 3.18 (s, 2H).

3. 3,4-Dibromo-N-methylaniline (7)

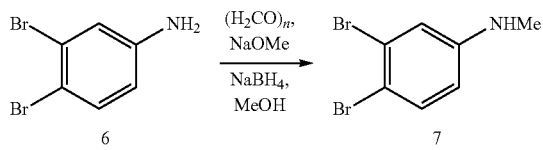 [SMILES: Nc1ccc(Br)c(Br)c1 ; CNc1ccc(Br)c(Br)c1]

To a solution of 3,4-dibromoaniline (6) (502 mg, 2.00 mmol) in methanol (20 mL) was added sodium methoxide (540 mg, 10.0 mmol) and the mixture was poured into a suspension of paraformaldehyde (120 mg, 4.00 mmol) in methanol (40 mL). The resulting mixture was stirred at ambient temperature under a nitrogen atmosphere for 8 h then heated at reflux for 8 h. Sodium borohydride (151 mg, 4.00 mmol) was added and the mixture was heated at reflux for 4 h. The reaction was quenched with saturated aqueous ammonium chloride solution (50 mL) and extracted with ethyl acetate (3×50 mL). The combined organic phases were dried (Na$_2$SO$_4$), and filtered. The solvents were removed under reduced pressure at water aspirator pressure and the crude product was purified by flash chromatography on silica gel (ethyl acetate/hexane, 5:95) affording 7 (130 mg, 0.491 mmol, 25%).

$^1$H NMR (400 MHz, CDCl$_3$) δ 7.32 (d, J=8.4 Hz, 1H), 6.83 (d, J=2.8 Hz, 1H) 6.40 (dd, 2.8 Hz, 1H), 3.79 (brs, 1H), 2.79 (s, 3H).

4. 3-[3,4-Dibromophenyl)methylamino]-3-oxopropanoic acid (9)

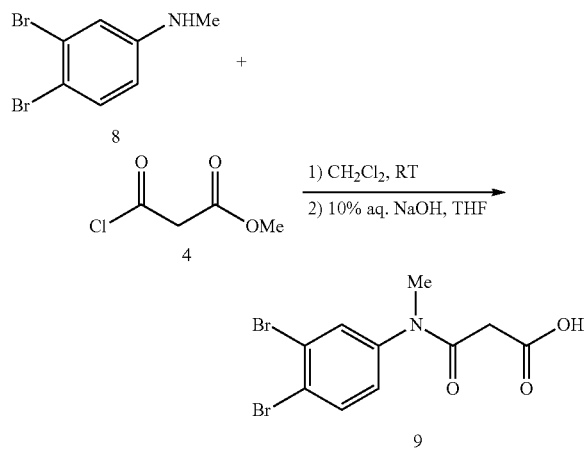

To a solution of 3,4-dibromo-N-methylaniline (8) (1.53 g, 5.77 mmol) in dichloromethane (20 mL) under a nitrogen atmosphere at ambient temperature was added methyl malonyl chloride (1.58 g, 11.5 mmol). The resulting mixture was stirred for 12 h followed by the addition of 2% HCl solution (aq., 15 mL). The mixture was extracted with dichloromethane (3×50 mL), the combined organic phase were dried (Na$_2$SO$_4$), filtered, and the solvent was removed under reduced pressure at water aspirator pressure.

The crude product was dissolved in tetrahydrofuran (25 mL) and treated with 10% aq. NaOH solution (20 mL) and the resulting mixture was stirred at ambient temperature for 12 h. The resulting mixture was washed with ether (3×20 mL) and the aqueous phase was treated with 6N HCl (aq.) until acidic (pH 2, pH paper). The acidic aqueous solution was extracted with ethyl acetate (3×20 mL). The combined organic phases were dried (Na$_2$SO$_4$), filtered, and the solvent was removed under reduced pressure at water aspirator pressure to afford pure 9 (1.34 g, 3.82 mmol, 66%).

$^1$H NMR (400 MHz, CDCl$_3$) δ 11.67 (brs, 1H), δ 7.70 (d, J=8.4 Hz, 1H), δ 7.52 (d, J=2.4 Hz, 1H) δ 7.08 (dd, J=8.8 Hz, 2.8 Hz, 1H), δ 3.28 (s, 3H), δ 3.20 (s, 2H).

Findings:

Same doses of N-MeDCPA took longer but looked as good as DCPA in OCL assay, and less toxic than DCPA. N-MeDCOPA shows inhibition of OCL formation at 100 μM.

Summary: Materials and Methods

Precursor and other test chemicals were obtained from commercial sources, such as, Sigma-Aldrich, ChemServices.

Cell lines were obtained from the American Type Culture Collection (ATCC).

Mice for CIA experiments will be obtained from commercial vendors, e.g., Charles River, Jackson Labs, etc.

We have shown that osteoclast maturation requires calcium-release activated calcium (CRAC) channels, both in vitro and in vivo. In inflammatory arthritis, osteoclasts mediate severe and debilitating bone erosion. In the current application, we disclose the value of CRAC channels as a therapeutic target to suppress bone erosion in acute inflammatory arthritis.

Methods: Collagen-induced arthritis (CIA) was induced in mice containing slow release pellets containing vehicle or the CRAC channel inhibitor 3,4-di chloropropionaniline (DCPA) one day prior to collagen II booster to induce arthritis. Effects on swelling, inflammatory cell invasion in joints, serum cytokines and bone erosion were measured.

Results:

Assays, by blinded observers, of arthritis severity in 11-12 replicates showed that DCPA, 21 mg/kg/day, suppressed arthritis development over three weeks. Bone and cartilage damage in sections of animal feet was reduced −50%; overall swelling of joints was reduced by a similar amount. Effects on bone density by μCT showed clear separation in DCPA treated CIA animals from CIA without treatment, while differences between controls without CIA and CIA treated with DCPA differed by small amounts and in most cases were not statistically different. Response was not related to anti-collagen titers. There were no adverse effects in the treated group on animal weight or activity, consistent with low toxicity. The effect was maximal 12-17 days after collagen booster, during the rapid appearance of arthritis in untreated CIA. At 20 days after treatment (day 40), differences in arthritis score were reduced and TNF-α, IL-1, or IL-6 in the serum of the animals were similar in treated and untreated animals.

Conclusion:

DCPA, a novel inhibitor of CRAC channels, suppresses bone erosion associated with acute arthritis in mice and might represent a new treatment modality for acute arthritis.

Acute arthritis occurs in solitary sites after trauma or can be caused by infections, such as in Lyme disease, in adults or children. Usually a cause is not identified (reference "1"). Rheumatoid arthritis (RA) typically has an inflammatory pattern indistinguishable from acute arthritis, but it has a chronic relapsing course leading to widespread destruction that involves many joints and usually requires lifelong therapy. While there are infectious causes and genetic predilections, typically RA also is idiopathic. Treatments for inflammatory arthritis include anti-metabolites, steroids, and TNF-α-blocking molecules that cause dangerous or debilitating side effects (2).

We arrived at calcium-release activated calcium current (CRAC) inhibitors as a potential new means to treat acute arthritis through a series of studies of the role of calcium in osteoclast development. We, and others, found that IP3R (receptor calcium channels in the ER) mediate osteoclast activity and differentiation (3) required for activation of the nuclear factor of activated T cells-1 (NFATcl) (4). Our studies on human or murine osteoclasts showed that suppression of CRAC components via siRNA or using a CRAC antagonist, 3,4-dichloropropionaniline reduced differentiation of bone degrading osteoclasts (5). Further, CRAC is required for normal T-cell differentiation, also via NFATcl activation (6). Thus a web of lymphocyte and macrophage differentiation events depend on CRAC, all of which might be involved in arthritis progression.

While total and long term suppression of CRAC is likely to cause severe developmental and immune defects (7), short term suppression of CRAC is unlikely to cause similar effects. Further, since CRAC is involved in T-cell response for tolerance (8, 9) as well as in osteoclast activation, we reasoned that partial CRAC inhibition by DCPA might effectively blunt acute arthritis. Although several CRAC inhibitors are known, we pursued DCPA in part because of very low toxicity; intermittent humans to DCPA in mg/kg quantities has minimal apparent toxicity (10), although massive doses, ~4-5 g/kg, can cause fatal methemoglobinemia (11).

We performed a trial of suppression of acute arthritis using controlled-release DCPA in mice with acute collagen-induced arthritis (CIA), at 10.5 or 21 mg/kg/day. DCPA caused a dramatic suppression of bone destruction and of articular inflammation at the higher dose. The studies used blinded observation of joint swelling over five weeks, and of sections of bone in the feet, as well as micro-CT In addition we studied anti-collagen antibodies and inflammatory cytokines, which did not correlate with arthritis response at the times studied, and were examined osteoclast and T-cell numbers in affected joints. Osteoclasts were reduced, although T-cells in sections were at similar density in inflammatory infiltrates in all groups.

Materials and Methods:

Animal Studies.

Male DBA/1 mice were used, from Harlan Laboratories, Frederick Md. Studies were approved by the Institutional Animal Care and Use Committee, Collagen induced arthritis was induced as described (12), with swelling in forelimb and hind limb joints studied in vivo, and histology and serology after sacrifice of the animals. Four untreated controls and 12 mice each with CIA without treatment (CIA/placebo) or with 10.5 mg/kg/day of DCPA (CIA/low dose DCPA) or 21 mg/kg/day of DCPA (CIA/high dose DCPA) were compared. Briefly, type II collagen (CII) was injected in complete Freund's adjuvant at 100 μg per animal (~4 μg/kg) at day 1 and, after 21 days, a booster dose of 100 μg C II in Freund's incomplete adjuvant. Inflammation was apparent 4-8 days after the second dose, in 80% of treated joints. At day 20 after primary immunization, subcutaneous time-release pellets containing DCPA, or the placebo, calibrated to release the stated doses for 21 days, were placed (Innovative Research of America, Sarasota Fla.). Mice were monitored for arthritis and scored in a blinded manner. Swelling of paws was be graded on scale from 0 to 4 indicating number of swollen digits. All paws were evaluated, so that the maximal arthritic index per mouse was 16. Additionally, hind paw swelling was measured using digital calipers on day 0, and each day on days 23-40. Analysis of the bones and joints for arthritis was done on H&E stained sections of hind paws, by blinded observation. This scored synovial expansion and inflammation, joint damage including pannus, and bone degradation, each on a scale of 0-3, with maximum score of 9. Due to losses during the experiment, 4 controls, 12 CIA mice without treatment, and 11 each mice with CIA and 10.5 or 21 mg/kg/day of DCPA were compared. For histological analysis, two paws from each animal were analyzed separately and blindly, and are calculated as two specimens per animal; however, if averages are used with n=animal number, there was no effect on differences (not shown).

Serum Analysis for Antibodies and Cytokines.

Heart blood at sacrifice, 40 days, was used for analysis. Plasma was separated by centrifiigation and frozen in aliquots at −20° C. until used. Production of anti-CII antibodies was evaluated by ELISA (Rheumera, Astarte Biologies, Redmond, Wash.). Production of cytokines was evaluated using V-PLEX panels in 96-well plates (Meso Scale Discovery, Rockville, Md.).

Antibody Labeling of Sections.

In sections from animals sacrificed at 37 days, effect of CIA and DCPA on osteoclast bone interface density was determined by anti-ATPa3 (TCIRG) labeling, and the effect on CD3 T cell density was determined using anti-CD3 labeling, using indirect antibody as described (13). Antibodies used were, for TCIRGI, mouse monoclonal (clone 6H3) antibody (Sigma-Aldrich) at 1:100 dilution. For CD3, anti-CD3 mouse monoclonal antibody (PC3/188A) against synthetic peptide spanning amino acids 156-168 of the cytoplasmic domain of human CD3-ε chain was used, at 1:100 dilution. Briefly, sections were blocked in PBS with 2% hydrogen peroxide for 5 minutes and then in PBS with 2% BSA for two hours, then reacted overnight with antibodies at indicated concentrations in PBS with 0.01% tween 20, and after washing with biotinylated anti-mouse at 1:1000 dilution. Then streptavidin-horseradish peroxidase, and diaminobenzidine substrate were added. Hematoxylin and eosin counterstain was use to show tissue features. Imaging used a Nikon TE2000 inverted microscope, with 14-bit 2048×2048 pixel monochrome CCD and RGB filters to reconstruct color (Spot, Sterling Heights, Mich.).

Micro-Computed Tomography and Morphometry.

Analysis by micro-computed tomography was as described (14). In brief, paws fixed in Millonig's solution were scanned on a Viva CT40 instrument (Scanco, Bassersdorf, Switzerland) with three-dimensional reconstruction by the manufacturer's instrument-specific software. The scan section increment was 20 μm; 3-D reconstruction used a density cutoff of 211 mg/cm$^3$. Analysis of trabecular thickness and trabecular spacing used the plate model.

Statistics.

Bar graphs show standard error of the mean. Statistical tests used were the analysis of variance (ANOVA) or Student's t-test as indicated. The alpha value to determine statistical significance was <0.05 or as otherwise indicated.

Results:

In Vivo Analysis of Collagen Induced Arthritis and the Effect of DCPA Treatment by Continuous-Release Subcutaneous Pellets.

Figure 1B:
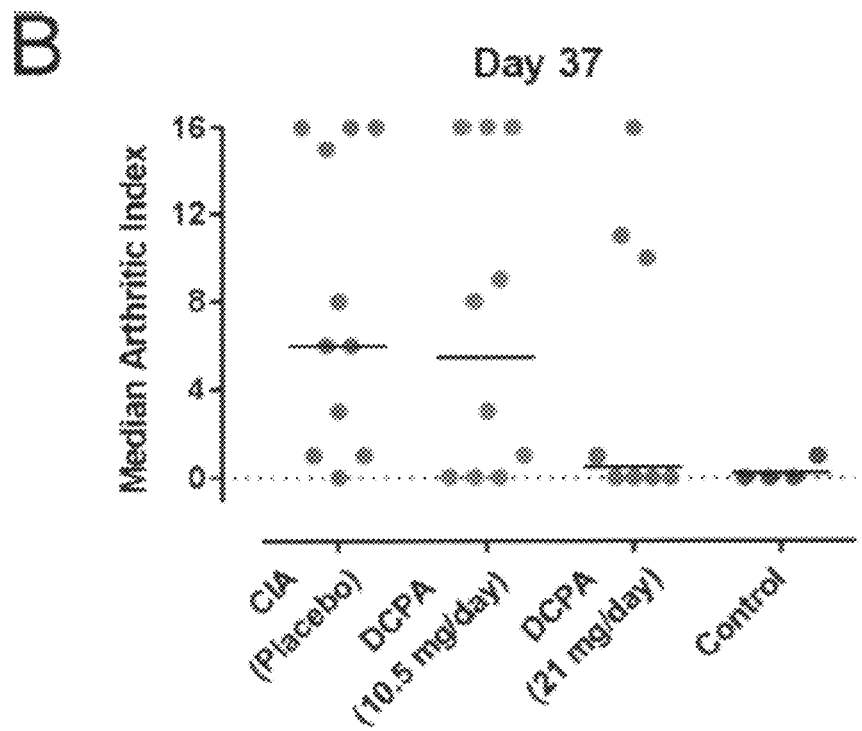
FIG. 1B is a scatter plot that shows the median effect of DCPA treatment by continuous-release subcutaneous pellets on collagen-induced arthritis as measured by the arthritic index.
Figure 11A:
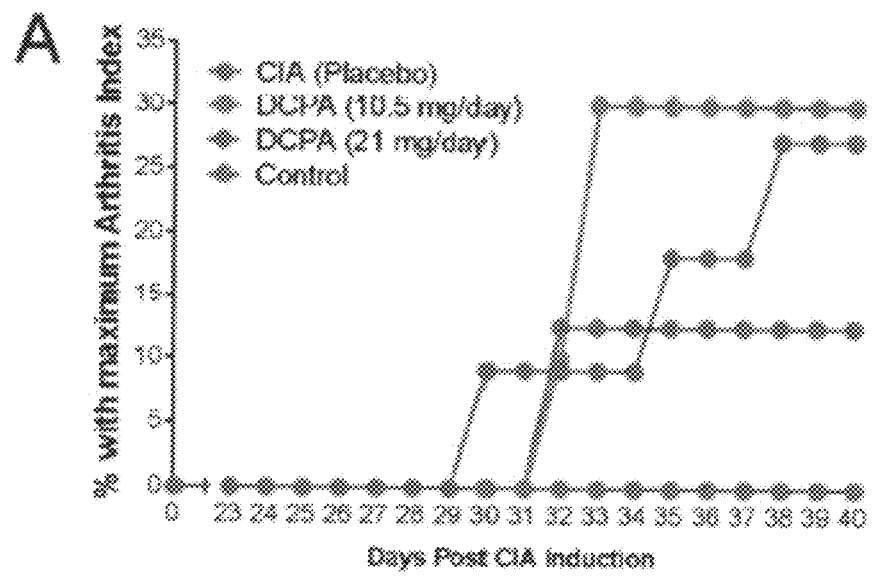
FIG. 11A shows the effect of DCPA treatment (10.5 mg/day DCPA, and 21 mg/day DCPA) by continuous release subcutaneous pellets on collagen-induced arthritic (CIA) as measured by the mean arthritis index.
Figure 11B:
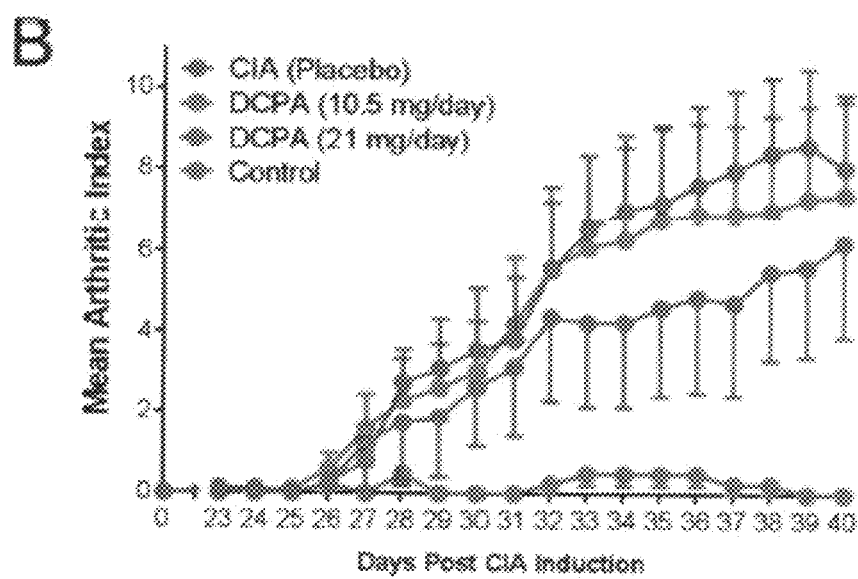
FIG. 11B shows the mean arthritis index for all groups. The CIA/placebo and low dose CIA/DCPA groups are essentially identical, whereas, the mean arthritic scores for the high dose CIA/DCPA groups was substantially lower than the previous two groups. As expected, the untreated control group showed zero to minimal arthritis indices.

Mice showed no changes on body weight, lethargy, or stress in any group, although severe inflammation of paws was induced by the CIA protocol. As measured by the arthritic index scoring each paw as 0-4 joints affected, using blinded observers from days 23-40 after second antigen injections at day 20, 80% of mice responded to collagen injections by induction of arthritis (FIG. 1). The effect of 10.5 mg/k/day of DCPA was modest and at most time points were not significant by ANOVA. On the other hand, 21 mg/kg/day of DCPA reduced the arthritic index, strongly before day 37 and 20-50% at days 38-40. The arthritic index of animals treated with 21 mg/kg/day were statistically different from the arthritic index measured in animals in which a placebo was used (p<0.01 by ANOVA). The untreated controls were also different from the CIA/placebo animals, P<0.001. A scatter plot of the scores of all animals on day 37 is shown in FIG. 1B. At sacrifice at 40 days, differences in arthritis scores were no longer significant (supplemental data), a possible factor in secondary measurements. In the CIA/placebo and low dose CIA/DCPA groups >50% of the animals showed arthritis scores that were equal to or above the mean. The majority of animals treated in the high dose CIA/DCPA group exhibited minimal arthritis scores, although 3 animals showed significant arthritis development. The fraction of animals with maximal arthritic involvement as well as the mean (±SEM) arthritis scores of all animals for the duration of the experiments are shown in FIGS. 11A and 11B and FIG. 12 (data). The relatively high variability shown likely reflects the all-or-none nature of arthritis; in the minority of mice treated with 21 mg/kg/day DCPA that developed arthritis, it was severe.

Analysis of Collagen Induced Arthritis in Sections of Feet.

Hind paws of animals were decalcified, paraffin embedded, cut, and stained with hematoxylin and eosin (FIGS. 2A-C). Variation in orientation of sections did not allow uniform measurement of thickness of synovium, and joints available for analysis varied. Therefore, blinded qualitative grading was used. The effect of 21 mg/kg/day of DCPA treatment on collagen induced arthritis at 40 days is shown in representative sections (FIGS. 2A-C). Arthritis was scored by a blinded observer on a scale of 0-9, evaluating two paws per animal, with all data shown in FIG. 2D, Sections were scored 0-3 for inflammation in periarticular tissue with 3 being suppurative inflammation, 0-3 for involvement of cartilage and the joint space, with 3 requiring a pannus, and 0-3 for degradation of periarticular bone, with 3 being full thickness destruction of the end plate. Examples of ankle bones in an untreated animal (FIG. 2A). High dose CIA/21 mg DCPA (FIG. 2B), showing measurable inflammation but not severe, and of severe arthritis in CIA/placebo (FIG. 2C) are shown. The quantification of severity of arthritis by a blinded observer is shown in FIG. 2D. The high dose DCPA/CIA group was statistically different from CIA/placebo group with p 0.024. The untreated group was statistically different from all other groups with p<0.01. Due to the poor separation of the low-dose treatment group (10.5 mg/kg/day) analysis of this gimp was omitted in most of the subsequent work. FIG. 2E shows the anti-type II collagen titers in the untreated control and CIA/placebo mice. Anti-CIA had a median titer of 32; although there appears to be a trend, titer was unrelated to arthritis severity by ANOVA. p=0.35; note that the variability is very high, with FIG. 2D showing standard error of the mean.

Histomorphometry.

Figure 13:
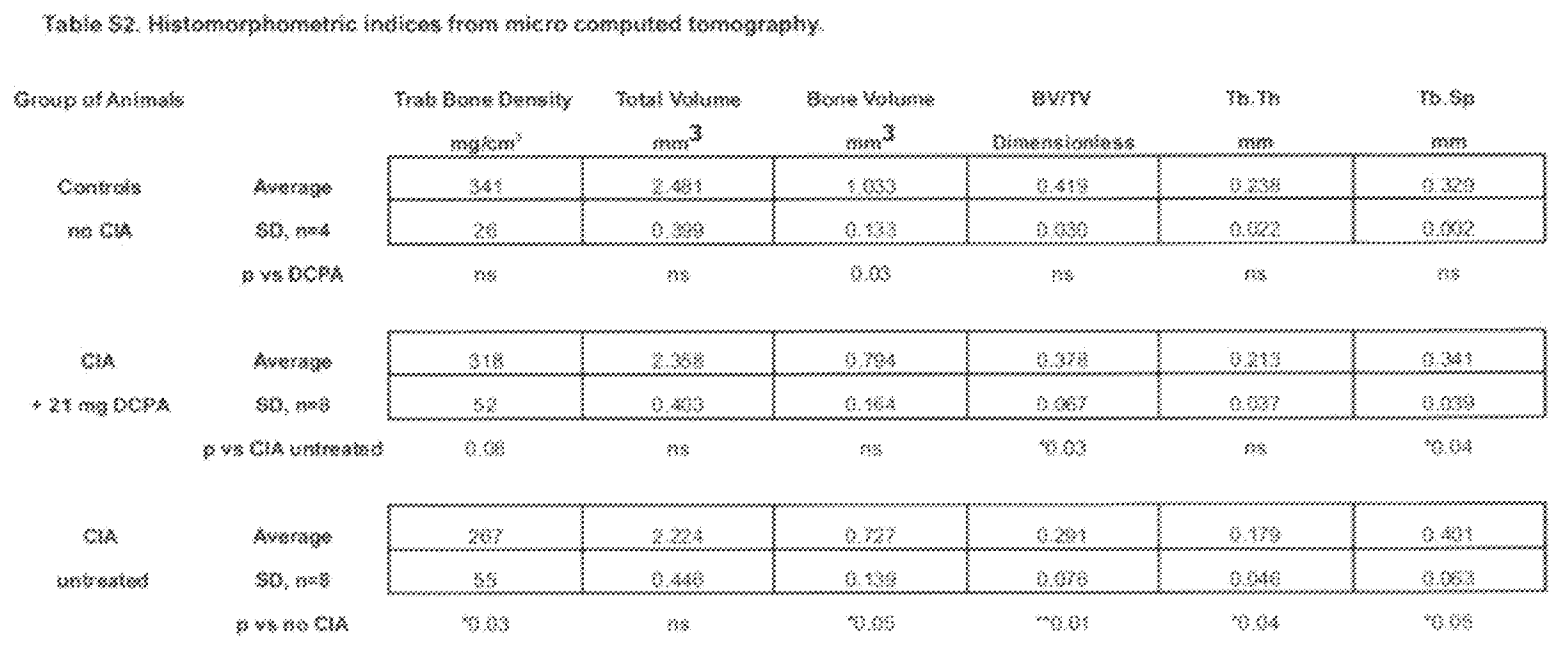

Micro-computed tomography revealed loss of bone in CIA/placebo animals (FIG. 3C), in accord with histology (FIGS. 2A-C); High dose CIA/DCPA (21 mg) could not be distinguished visually from untreated controls. Low dose CIA/DCPA (10.5 mg/kg/day) were not studied. Quantitative morphometry showed that bone density and bone volume per total volume was significantly decreased in CIA/placebo mice. The high dose CIA/DCPA treatment had density indistinguishable from untreated controls (FIG. 3D) and showing a trend to increase relative to CIA without treatment (p–0.08). In bone volume/total volume, CIA/DCPA treated bone was not different from the untreated controls, and was statistically greater than CIA/placebo animals p=0.03. Other parameters of bone morphometry including trabecular thickness and trabecular spacing showed consistent differences, with DCPA treatment in all cases intermediate between the CIA group, which had bone loss, and the no CIA controls, in some cases with no significant difference between DCPA treated CIA and no CIA controls. These data are shown in FIG. 13. This is consistent with a protective effect of DCPA against bone loss despite cytokine production secondary to CIA.

Effect of CIA with and without DCPA Treatment on Serum Inflammatory Cytokines.

We determined the effect of DCPA treatment on key serum cytokines including TNF-α, IL-1, and IL-6. The results showed strong induction of the cytokines by CIA but, surprisingly, showed no effect of DCPA on cytokine production despite strong suppression of arthritis by DCPA (FIGS. 1A-B, 2A-E, and 3A-E). Representative data from one of two separate analyses with essentially identical results is shown in FIGS. 4A-E. Results for Interferon (INF) gamma, CXCL1, INF-γ, IL-1β, and IL-6 are shown (FIGS. 4A-E). All of the cytokines shown were induced strongly with the exception of CXCL1, which was marginally different between untreated controls and the CIA/placebo and high dose CIA/DCPA (p=0.06), and no cytokines differed between CIA/placebo and high dose CIA/DCPA groups. Individual groups of CIA/placebo or CIA/DCPA had variably significant differences with the untreated controls as indicated in FIGS. 4A-E. FIGS. 4A-E show one of two multiplex assays with similar results is shown. All of the cytokines shown were induced strongly with the exception of CXCL1, which was marginally different in untreated controls and CIA (p–0.06), and no cytokines differed between CIA/placebo and CIA/DCPA treated with 21 mg/kg/day of DCPA. **p<0.01 or exact P value shown; *, p<0.05. P values versus all CIA indicate the difference of the untreated control with the combined CIA groups. Based on these data, we hypothesize that the mechanism, reversible inhibition of CRAC activity in osteoclast development, is likely to be independent of arthritis treatments that inhibit inflammatory cytokine production, a potential advantage of DCPA therapy. DCPA did not significantly affect cytokine production of IL-12p70 or IL-10, which also were measured. Sera tested had IL-17 levels too low for meaningful comparisons.

Effect of CIA and DCPA on Osteoclasts and T Cells in Tissue Sections.

Antibody labeling for ATPa3 was used to determine the effect of the DCPA treatment on osteoclasts in tissue (FIGS. 5A-D). This target is the large subunit of the osteoclast-specific membrane hydrogen pump, and is not expressed by macrophages; enzymes including cathepsin K and TRAP are highly expressed by osteoclasts often used as osteoclast markers, but these are also expressed in macrophages, and so are less specific (28,29). This showed a large and statistically significant reduction in the osteoclast surface area of high dose C1A/DCPA, relative to CIA/placebo, in keeping with the differences shown in FIG. 2. We also labeled bone with anti-CD3 to show T lymphocytes (FIGS. 5E-H). This showed that the density of T cells in inflammatory infiltrates was similar in CIA/placebo and CIA/DCPA groups.

We report the first in vivo trial of a calcium release activated calcium current (CRAC) inhibitor on inflammatory arthritis using the mouse collagen induced arthritis model (12). The theoretical basis for the observed effect is that CRAC currents are essential to normal osteoclast development, and also are involved in T cell activation which also promotes arthritis (5,6). Our results include a highly significant decrease in joint swelling, inflammatory infiltrate, and bone damage. These effects were independent from suppression of serum cytokines, suggesting that the approach may complement therapy that targets the inflammatory cytokines. The effects on many bone density and trabecular bone parameters showed uniformly that DCPA reduced the effects of CIA on bone health, although there was variability in statistical significance between individual parameters. In trabecular bone density, bone volume/total volume, and trabecular spacing, the controls without were not statistically different from CIA treated with 21 mg/kg of DCPA, but CIA without treatment was well separated statistically from controls without CIA (FIGS. 3A and 13).

The pore-forming unit of the CRAC channel is Orail (15), a four transmembrane-containing protein in the plasma membrane that is activated primarily by the endoplasmic-reticulum (ER) calcium sensor STIM1 (8). Hence, in response to ER $Ca^{2+}$ depletion, STIM1 translocates within the ER towards regions of close PM apposition where it interacts with Orail (16). Using electrophysiological CRAC measurement and fluorescence analysis of STIM1/Orail association, we determined that DCPA inhibits CRAC channel activation by destabilizing STIM1/Orail interaction, leading to CRAC channel closure (Id. Zhou et al., 2011). In that study, we further showed that DCPA inhibits osteoclast formation in vitro; we now show that that DCPA-induced CRAC channel inhibition leads to inhibition of osteoclast formation and function in vivo in an arthritis model.

Human Orail defects are now known, and are associated with defects including hypocalcemia and muscular abnormalities (17). Although our mouse model showed no signs of serious metabolic or muscular anomaly, in larger animal studies it will be important to monitor these parameters. Oddly, some Orail polymorphisms also are associated with increased serum calcium and kidney disease, although the mechanisms are unclear (18). A dysfunctional Stim1 mutation, that is, in the calcium sensor required to activate Orail complexes, causes a syndrome with multiple developmental defects including anemia, asplenia, myopathy, and ichthyosis (19). Orail is also implicated in respiratory and neural development (20, 21); in humans as in mice (7), complete absence of CRAC is probably lethal during early development or soon after birth. However, after normal development, at least for a time frame of 3-4 weeks, suppression of CRAC appears to be relatively benign.

Analysis of inflammatory cytokines showed that DCPA treatment at 21 mg/kg/day did not affect TNF-α, IL-1, IL-6, CXCL1, and IFN-γ (FIG. 4) all of which were upregulated 2.5 to >10 fold by the collagen induced arthritis. We did not detect significant IL-17; other work has shown that IL-17 after adjuvant induced arthritis, at 35 days, had serum concentrations <1 ng/ml 35 days after arthritis induction, and which varied only –20% between untreated animals and arthritic animals (22), so it is likely our assay was insufficiently sensitive to determine IL-17 effects. There is strong evidence for the involvement of IL-17 in cellular signaling involved in induction of arthritis (23,24,25,26), but it is not a major secreted serum protein; indeed, some amount of Orail signaling is believed to be required to support TH17 cell development (27). Typically, XL-17 production is assayed in tissue sections or cells, and further work will be needed to resolve the contribution of IL-17 suppression to the reduction of arthritis severity.

Recently, it was reported that another inhibitor of store-operated calcium entry (SOCE), 4-methy-4-[3,5-bis(trifluo-rometliyl)-1H-pyrazol-1-yl]-1,2,3-thiadiazole-5-carboxa-nilide, also called YM-58483 or BTP-2. at 10 mg/kg suppressed CIA and suppressed inflammatory cytokines IL1, IL6, and TNF-α to near-baseline levels at 10 days after induction (30). While it is expected that other inhibitors of CRAC channels would function similarly in suppressing arthritis, the differences in response of inflammatory cytokines are very interesting, although not unexpected. The inhibitor BTP2 suppresses cytokines including 1L2 and calcium influx by other calcium channels, specifically TRPM4, at low nanomolar concentrations (31). Overall, it is likely that BTP2 effects overlap those of DCPA, but that BTP2 has a range of effects that may be, at least in part, unrelated to CRAC suppression. It will be important to test additional time points to determine if DCPA has effects on some cytokines that were not resolved, but, importantly, at a time when skeletal effects were clearly suppressed by DCPA (see FIGS. 12 and 13), IL1, IL6, and TNF (were essentially identical in CIA with and without DCPA treatment (FIGS. 4A-E).

Figure 6:
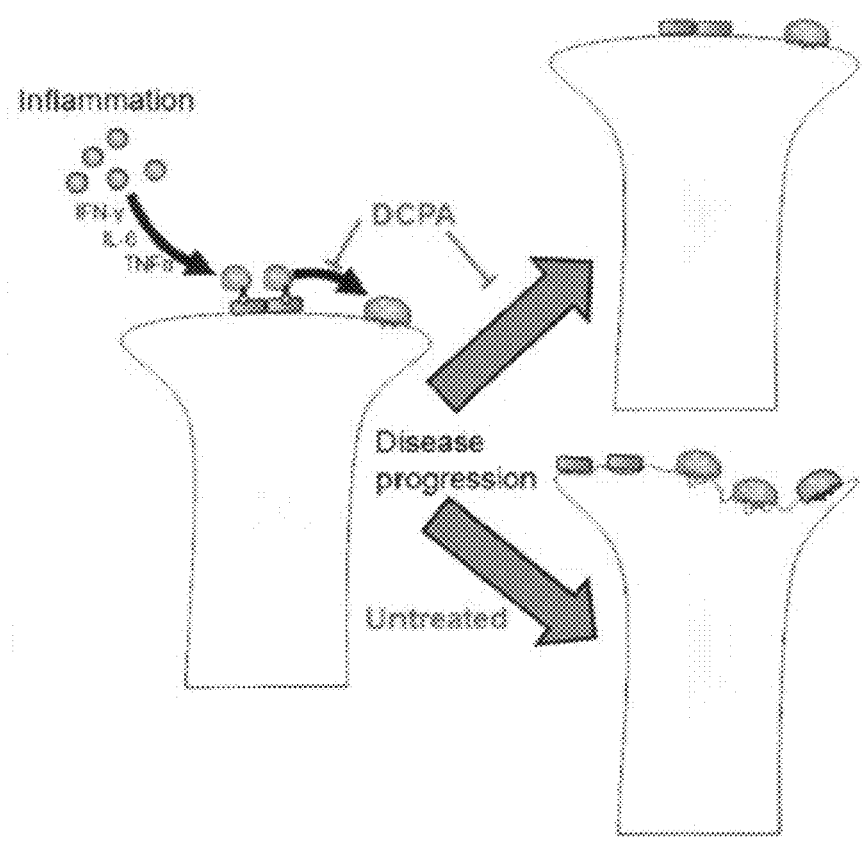
FIG. 6 is a model that shows the key functions of DCPA responsible for inhibiting collagen induced acute arthritis (CIA). Independently of cytokines, the CRAC-inhibitor DCPA blocks maturation.

The clear effect of DCPA treatment on arthritis, despite no change in serum inflammatory factors, suggests that the direct blockade of CRAC activity by DCPA mediates the reduction in osteoclast maturation. This model (FIG. 6) will require further testing and refinement. However, the independence of the DCPA effect from suppression of serum inflammatory cytokines suggests that Orail antagonists may be valuable modalities for treating inflammatory arthritis, and possibly rheumatoid arthritis, by a mechanism essentially independent of inflammatory cytokine suppression. It is likely that long-term strong inhibition of CRAC would result in severe immunological or bone effects, based on the knockout mouse phenotype (7), but treatment for several weeks had no effect on animal health, activity, or weight.

In conclusion, treatment of collagen induced arthritis with 21 mg/kg/day of 3,4-dichloropropionaniline dramatically suppressed bone erosion and bone loss by micro-computed tomography that is associated with collagen induced arthritis, with no apparent effect on the general health of the animals or the increase in serum inflammatory growth factors characteristic of acute arthritis. This remarkable ability of a CRAC channel inhibitor to regulate bone erosion without interfering with immune function may lead to a valuable new tool for the treatment of inflammatory arthritis.

Figure 7A:
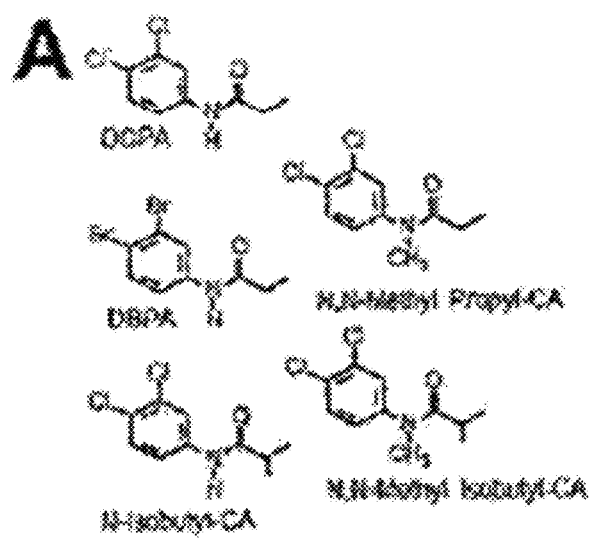
FIG. 7A shows the structures of analogs of DCPA.

FIG. 7A shows the structures of analogs of DCPA. DCPA analogs are designed to eliminate metabolism into toxic DCA compounds.

Figure 7B:
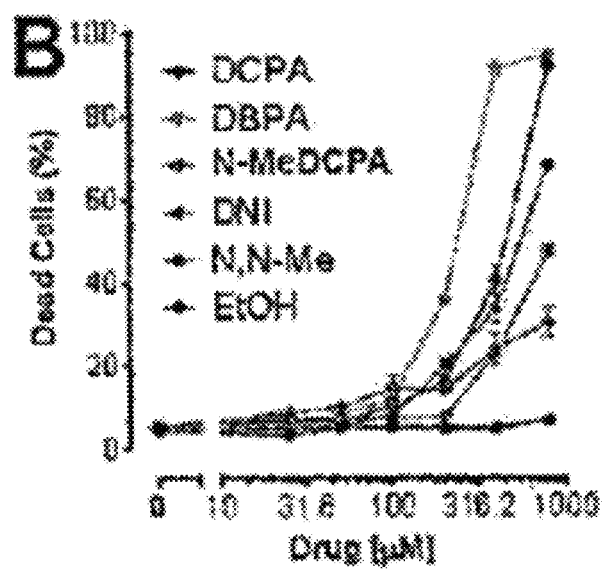
FIG. 7B shows the toxicity of DCPA and DCPA analogs on cells.
Figure 7C:
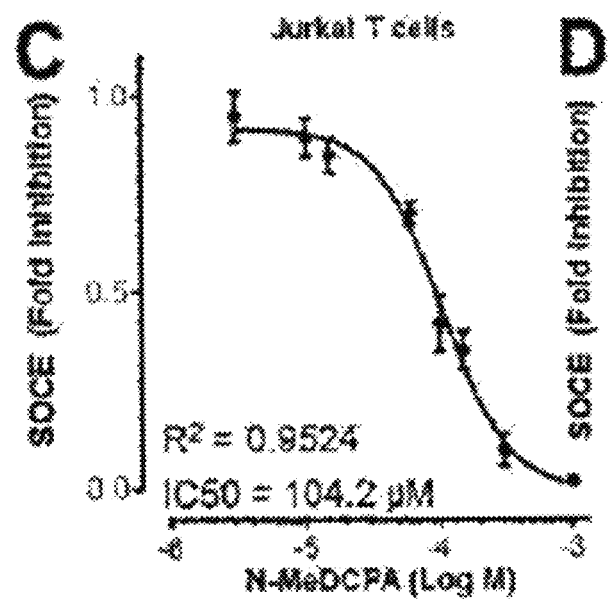
FIG. 7C shows Jurkat T cells loaded with Fura-2 followed by SOCE measurement.

FIG. 7B shows the toxicity of DCPA and DCPA analogs on cells. Toxicity was assessed by 7-AAD staining of Jurkat T cells incubated overnight in each analog at the indicated concentration FIG. 7C shows Jurkat T cells loaded with Fura-2 followed by SOCE measurement via microscopy.

Figure 7D:
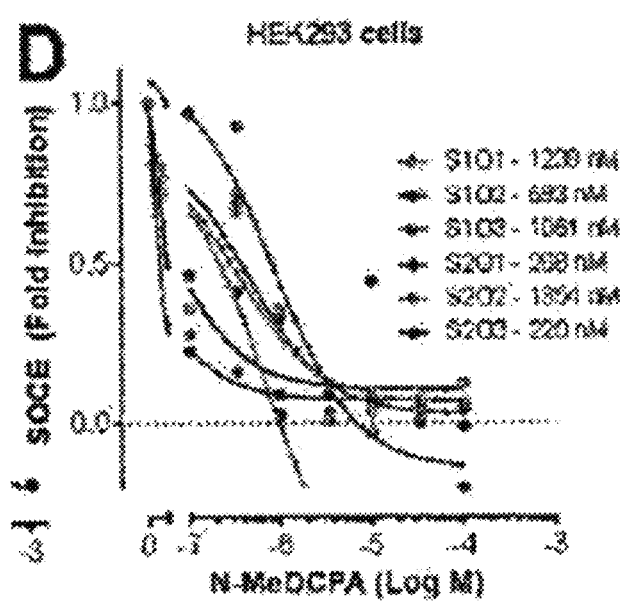
FIG. 7D shows HEK293 cells overexpressing each combination of STIM and Orai1 were loaded with Fluo-4 followed by SOCE measurement.

FIG. 7D shows HEK293 cells overexpressing each combination of STIM and Orail were loaded with Fluo-4 followed by SOCE measurement on the Hamamatsu μCell. Two curves fall below zero because there is less $Ca^{2+}$ present at the end of the experiment (i.e. celles contain a low level of $Ca^{2+}$ before starting the experiment).

Figure 8:
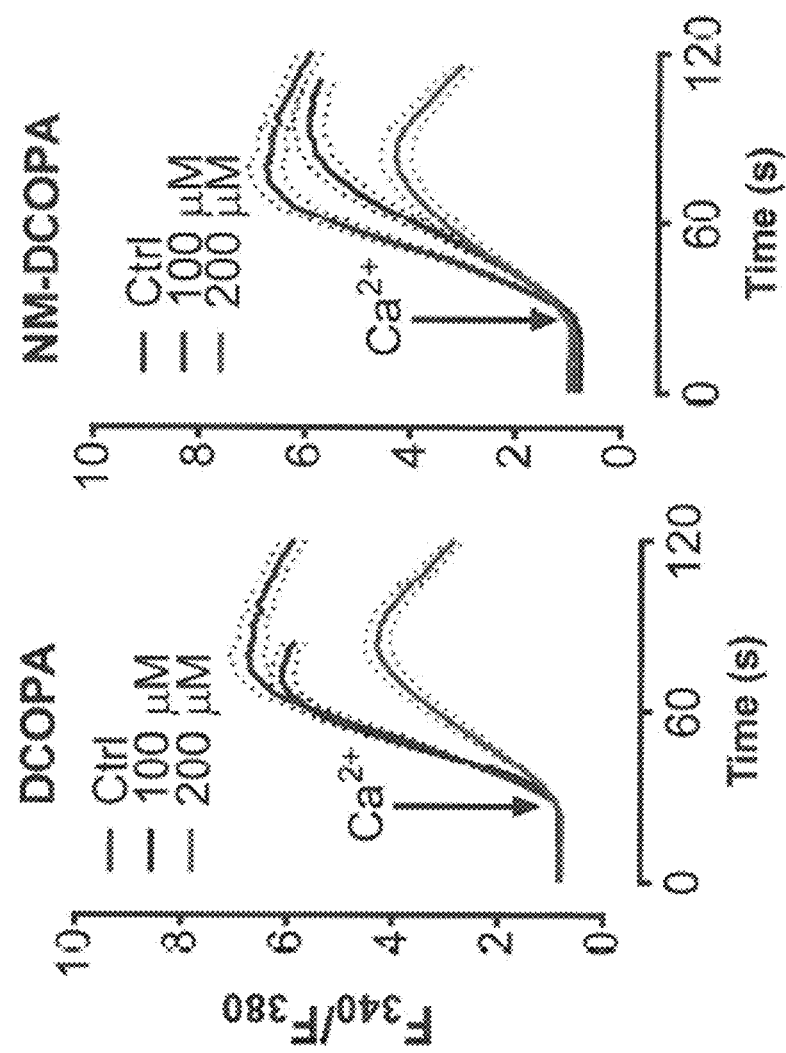
FIG. 8 shows SOCE in Fura-2 Loaded Jurkat T Cells for compounds DCOPA and NM-DCOPA of this invention. Cells were treated with Thapsigargin (2 μM) for ten (10) minutes prior to time 0.

FIG. 8 shows SOCE in Fura-2 Loaded Jurkat T Cells for compounds DCOPA and NM-DCOPA (i.e. N-methyl-DCOPA) of this invention. Cells were treated with Thapsigargin (2 μM) for ten (10) minutes prior to time 0.

Figure 9:
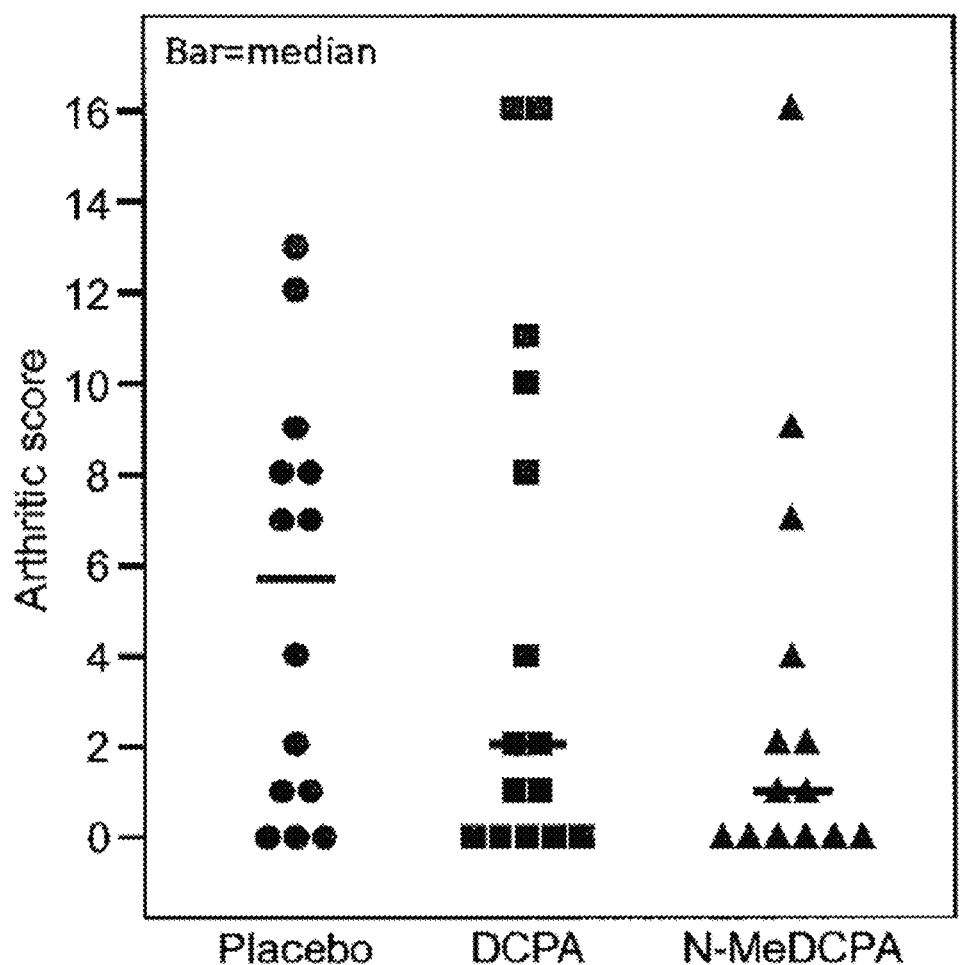
FIG. 9 shows the arthritis score comparison for placebo, DCPA, and N-MeDCPA at 35 days.

FIG. 9 shows the arthritis score comparison for placebo, DCPA, and N-MeDCPA at 35 days.

FIG. 10 shows the apoptosis data for NMe-DCOPA (i.e., N-methyl-DCOPA, and identified in FIG. 10 as NMD-COPA).

FIG. 11A shows the effect of DCPA treatment (10.5 mg/day DCPA, and 21 mg/day DCPA) by continuous release subcutaneous pellets on collagen-induced arthritis (CIA) as measured by the mean arthritis index. FIG. 11 A shows the fraction of animals with maximal arthritis scores. This demonstrates the efficacy of CIA induction (top trace), and the data of FIG. 11A shows the treatment failure-proportion in treated groups.

FIG. 11B shows the mean arthritis index for all groups. The CIA/placebo and low dose CIA/DCPA groups are essentially identical, whereas, the mean arthritic scores for the high dose CIA/DCPA groups was substantially lower than the previous two groups. As expected, the untreated control group showed zero to minimal arthritis indices. The data were gathered by a blinded observer. N=4 for untreated controls; N=11 for CIA/placebo; N=10 for the low dose CIA/DCPA treated group; N=8 for the high doses C1A/DCPA treated group. Error bars are omitted for clarity; CIA/placebo was statistically different from high dose CIA/DCPA by ANOVA (p<0.01) and different from the CIA/placebo controls (p<0.001).

Figure 12A:
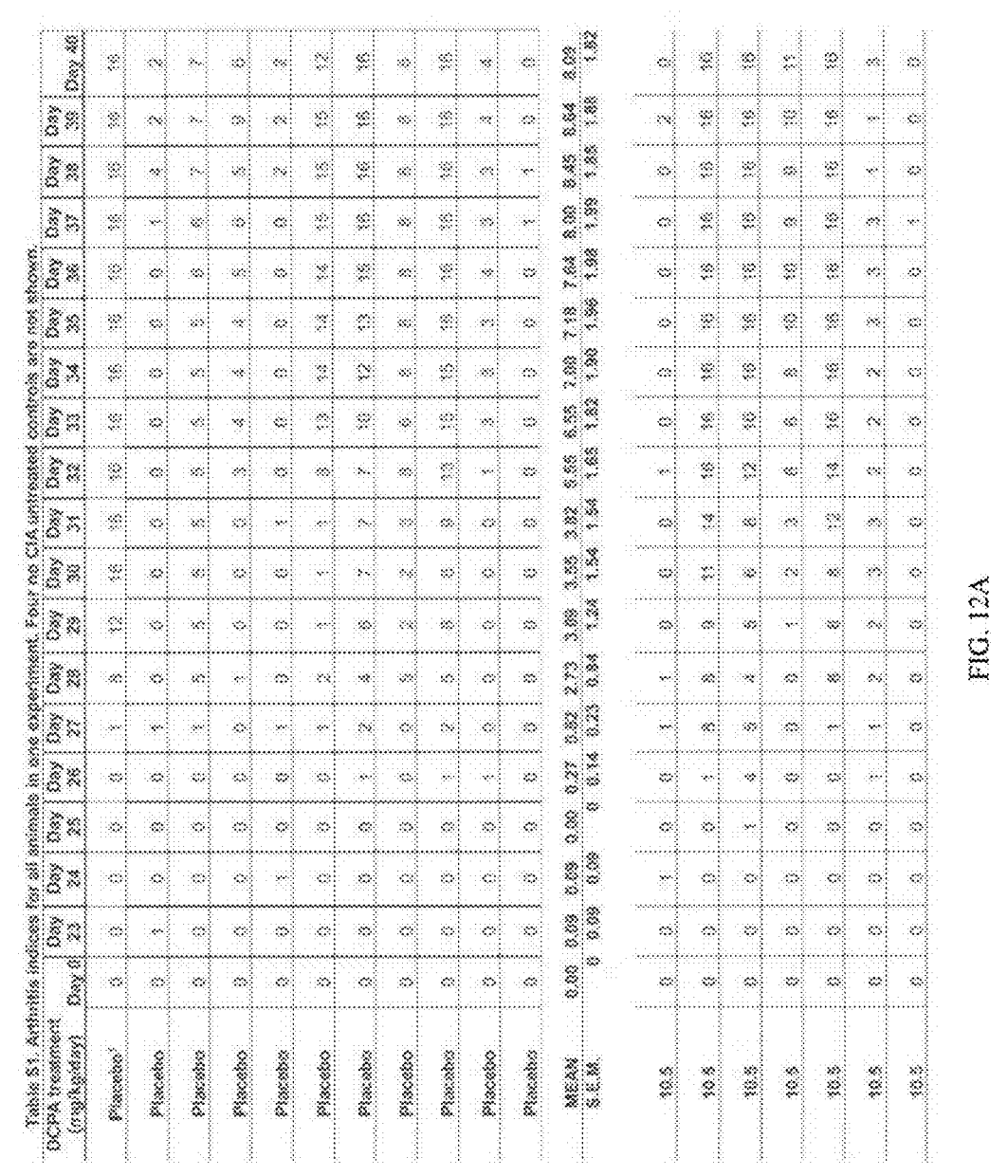
Figure 12B:
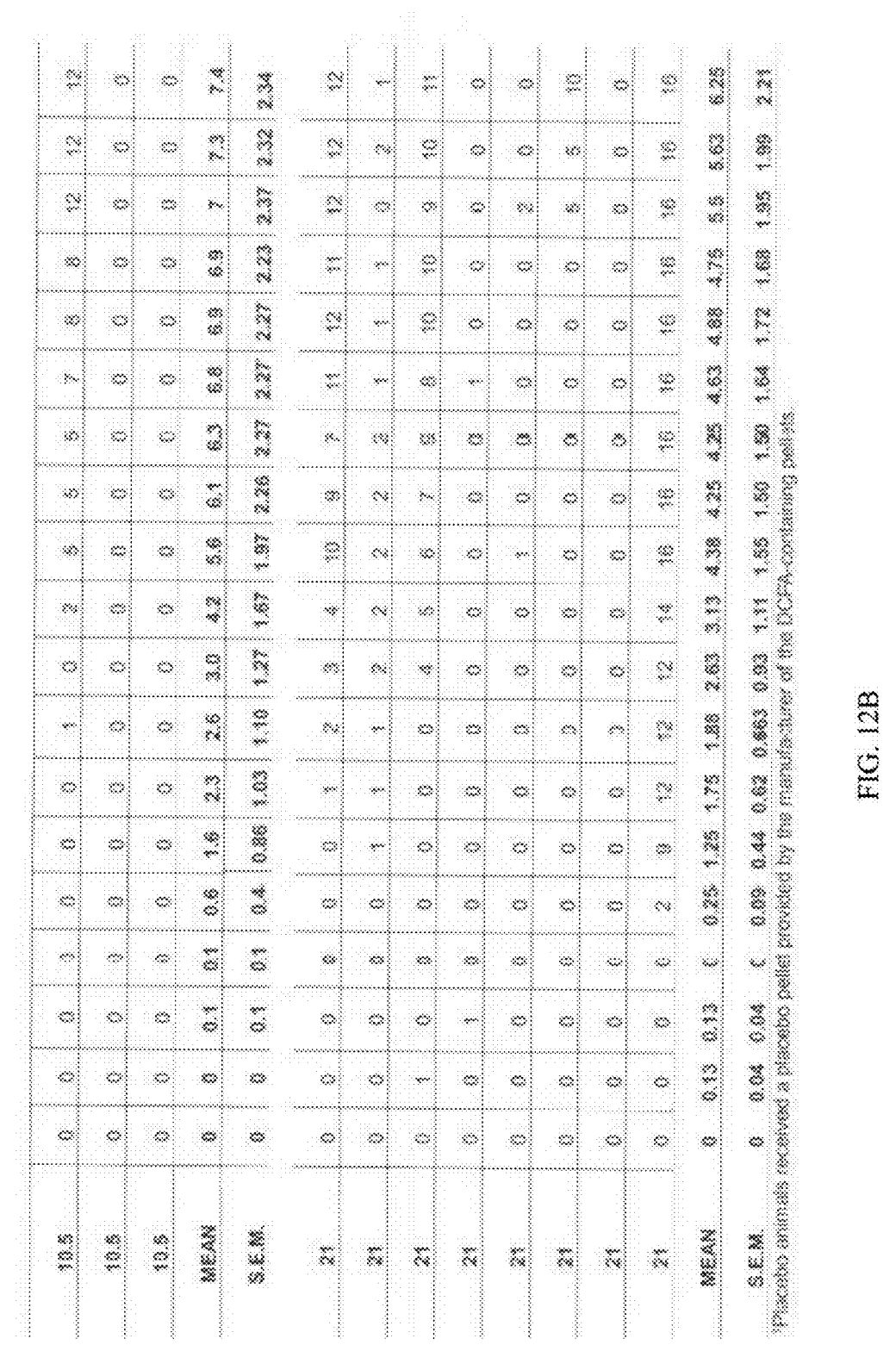

FIGS. 12A and 12B show data of arthritis indices for all animals in one experiment of treatment with placebo (inert composition), 10.5 mg/day DCPA treatment, and 21 mg/da DCPA treatment, respectively.

FIG. 13 shows data of histomorphometric indices from micro computed tomography of controls and no CIA, CIA and 21 mg DCPA treatment, and CIA and untreated group of animals.

REFERENCES

1. Till S H, Snaith M L. Assessment, investigation, and management of acute monoarthritis. J Accid Emerg Med 1999; 16: 355-61.
2. Gaffo A, Saag K G Curtis J R. Treatment of rheumatoid arthritis. Am J Health Syst Pharm 2006; 63: 2451-65.
3. Yaroslayskiy B B, Turkova I, Wang Y, Robinson L J, Blair H C. Functional osteoclast attachment requires inositol-1,4,5-trisphosphate receptor-associated cGMP-dependent kinase substrate. Lab Invest 2010; 90: 1533-42.
4. Negishi-Koga T, Takayanagi H. $Ca^{2+}$-NFATcl signaling is an essential axis of osteoclast differentiation. Immunol Rev 2009; 231: 241-56.
5. Zhou Y, Lewis T L, Robinson L J, Brundage K M, Schafer R, Martin K H, et al. The role of calcium release activated calcium channels in osteoclast differentiation. J Cell Physiol 2011; 226: 1082-9.
6. Yue C, Soboloff J, Gamero A M. Control of type I interferon-induced cell death by Orail-mediated calcium entry in T cells. J Biol Chem. 2012; 287: 3207-16.
7. Robinson L J, Mancarella S, Songsawad D, Tourkova I L, Bamett J B, Gill D L, Soboloff J, Blair H C. Gene disruption of the calcium channel Orail results in inhibition of osteoclast and osteoblast differentiation and impairs skeletal development. Lab Invest 2012; 92: 1071-83.
8. Soboloff J, Rothberg B S, Madesh M, Gill D L. STIM proteins: dynamic calcium signal transducers. Nat Rev Mol Cell Biol 2012; 13: 549-65.
9. Qu B, Al-Ansary D, Kummerow C, Hoth M, Schwarz E C. ORAI-mediated calcium influx in T cell proliferation, apoptosis and tolerance. Cell Calcium 2011; 50: 261-9.
10. Corsini E, Codeca I, Mangiaratti S, Birindelli S, Minoia C, Turci R, et al. Immunomodulatory effects of the herbicide propanil on cytokine production in humans; In vivo and in vitro exposure. Toxicol Appl Pharmacol. 2007; 222: 202-10.
11. Ranasinghe P, Dilrukshi S A, Atukorala I, Katulanda P, Gnanathasan A. Exchange transfusion can be life-saving in severe propanil poisoning: a case report. BMC Res Notes. 2014; 7: 700.
12. Clutter S D, Wilson D C, Marinov A D, Hirsch R. Follistatin-like protein 1 promotes arthritis by up-regulating IFN-gamma. J Immunol 2009; 182: 234-9.
13. Cackowski F C, Anderson J L, Patrene K D, Choksi R J, Shapiro S D, Windle J J, et al. Osteoclasts are important for bone angiogenesis. Blood 2010; 115: 140-9.
14. Tondelli B, Blair H C, Guerrini M, Patrene K D, Cassani B, Vezzoni P, et al. Fetal liver cells transplanted in utero rescue the osteopetrotic phenotype in the oc/oc mouse. Am J Pathol 2009; 174: 727-35.
15. Prakriya M, Feske S, Gwack Y, Srikanth S, Rao A, Hogan P G. Orail is an essential pore subunit of the CRAC channel. Nature 2006; 443: 230-3,
16. Roberts-Thomson S J, Peters A A, Grice D M, Monteith G R. ORAI-mediated calcium entry: mechanism and roles, diseases and pharmacology. Pharmacol Ther 2010; 127:121-30.
17. Endo Y, Noguchi S, Hara Y, Hayashi Y K, Motomura K, Miyatake S, et al. Dominant mutations in ORAI1 cause tubular aggregate myopathy with hypocalcemia via constitutive activation of store-operated $Ca^{2+}$ channels. Hum Mol Genet 2014 Sep. 16 [Epub ahead of print].
18. Hwang D Y, Chien S C, Hsu Y W, Kao C C, Cheng S Y, Lu H C. et al. Genetic polymorphisms of ° RAH and chronic kidney disease in Taiwanese population. Biomed Res Int 2014; 2014; 290863.
19. Misceo D, Holmgren A, Louch W E, Holme P A, Mizobuchi M, Morales R J, et al. A dominant STIM1 mutation causes Stormorken syndrome. Hum Mutat. 2014; 35: 556-64.
20. Samanta K, Bakowski D, Parekh A B. Key role for store-operated Ca2+ channels in activating gene expression in human airway bronchial epithelial cells. PLoS One 2014; 9: el 05586.
21. Somasundaram A, Shum A K, McBride H J, Kessler J A, Feske S, Miller R J, et al. Store-operated CRAC channels 22. Song S S, Huang B, Wang Q T, Wu Y J, Fu J J, Zhang Y F, et al. BF02, a recombinant TNFR2 fusion protein, alleviates adjuvant arthritis by regulating T lymphocytes in rats. Acta Pharmacol Sin 2013; 34: 414-23.
23. Criado G Risco A, Alsina-Beauchamp D, Perez-Lorenzo M J, Escos A, Cuenda A. Alternative p38 MAPKs are essential for collagen-induced arthritis. Arthritis Rheumatol 2014; 66: 1208-17.
24. Marijnissen R J, Roeleveld D M, Young D, Nickerson-Nutter C, Abdollahi-Roodsaz S, Garcia de Aquino S, et al. Interleukin-21 receptor deficiency increases the initial toll-like receptor 2 response but protects against joint pathology by reducing Th1 and Th17 cells during streptococcal cell wall arthritis. Arthritis Rheumatol 2014; 66: 886-95.
25. Raychaudhuri S P. Role of IL-17 in psoriasis and psoriatic arthritis. Clin Rev Allergy Immunol 2013; 44: 183-93.
26. Li J, Hsu H C, Mountz J D. The Dynamic Duo-Inflammatory M1 macrophages and Th17 cells in Rheumatic Diseases. J Orthop Rheumatol 2013; 1:4.
27. Kim K D, Srikanth S. Tan Y V, Yee M K, Jew M, Damoiseaux R, et al. Calcium signaling via Orai1 is essential for induction of the nuclear oiphan receptor pathway to drive Th17 differentiation. J Immunol 2014; 192; 110-22.
28. Miiller S, Faulhaber A, Sieber C, Pfeifer D, Hochberg T, Gansz M, Deshmukh S D, Dauth S, Brix K, Saftig P, Peters C, Hennekc P, Reinheckel T. The endolysosomal cysteine cathepsins L and K are involved in macrophage-mediated clearance of *Staphylococcus aureus* and the concomitant cytokine induction. FASEB J. 2014; 281: 162-75.
29. Kehely A, Moss D W. Circulating levels of tartrate-resistant acid phosphatase in macrophage-activated lung disease. Ann Clin Biochem. 1992; 29:172-5.
30. Gao X, Gao R, Tian Y, et al. A store-operated calcium channel inhibitor attenuates collagen-induced arthritis. Br J Pharmacol. 2015 Feb. 5. doi: 10.1111/bph.13104. [Epub ahead of print]
31. Takezawa R, Cheng H, Beck A, et al. A pyrazole derivative potently inhibits lymphocyte Ca2+ influx and cytokine production by facilitating transient receptor potential melastatin 4 channel activity. Mol Pharmacol. 2006; 69: 1413-20.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A compound that is selected from the group consisting of N-methyl 3-(3,4-dichloroanilino)-3-oxopropanoic acid; N,2-dimethyl 3-(3,4-dichloroanilino)-3-oxopropanoic acid; 2-methyl 3-(3,4-dichloroanilino)-3-oxopropanoic acid; isobutyl 3-(3,4-dichloroanilino)-3-oxopropanoic acid; and N-methyl-isobutyl 3-(3,4-dichloroanilino)-3-oxopropanoic acid.

* * * * *